US009549813B2

(12) United States Patent
Anderson et al.

(10) Patent No.: US 9,549,813 B2
(45) Date of Patent: Jan. 24, 2017

(54) INSERTER CAP AND RELATED FEATURES

(75) Inventors: Steven R. Anderson, Rancho Santa Margarita, CA (US); Mark S. Cole, Trabuco Canyon, CA (US)

(73) Assignee: ABBOTT MEDICAL OPTICS INC., Santa Ana, CA (US)

( * ) Notice: Subject to any disclaimer, the term of this patent is extended or adjusted under 35 U.S.C. 154(b) by 881 days.

(21) Appl. No.: 13/818,550

(22) PCT Filed: Aug. 24, 2011

(86) PCT No.: PCT/US2011/049030

§ 371 (c)(1),
(2), (4) Date: Jun. 13, 2013

(87) PCT Pub. No.: WO2012/027518

PCT Pub. Date: Mar. 1, 2012

(65) Prior Publication Data

US 2014/0296863 A1    Oct. 2, 2014

Related U.S. Application Data

(60) Provisional application No. 61/376,661, filed on Aug. 24, 2010, provisional application No. 61/467,584, (Continued)

(51) Int. Cl.
*A61F 2/16*    (2006.01)
(52) U.S. Cl.
CPC ............. *A61F 2/167* (2013.01); *A61F 2/1662* (2013.01); *A61F 2/1667* (2013.01); *A61F 2/1675* (2013.01); *A61F 2/1678* (2013.01)
(58) Field of Classification Search
CPC ...... A61F 2/167; A61F 2/1667; A61F 2/1675; A61F 2/1662; A61F 2/1678; A61B 5/150351; A61B 5/1411; A61B 17/32093; A61B 2017/32113; A61B 17/3494; A61B 2017/347; B65D 41/00; B65D 41/0471; B65D 41/0485; B65D 41/0492; B65D 41/62; B65D 41/16

See application file for complete search history.

(56) References Cited

U.S. PATENT DOCUMENTS 4,619,656 A    10/1986 Lindstrom
4,681,102 A    7/1987 Bartell
(Continued)

FOREIGN PATENT DOCUMENTS

BE    1016692 A3    4/2007
CN    1681457 A    10/2005
(Continued)

OTHER PUBLICATIONS

International Search Report and Written Opinion for Application No. PCT/US2011/049029, mailed on Jul. 12, 2012, 13 pages.
(Continued)

*Primary Examiner* — Elizabeth Houston
*Assistant Examiner* — Rachel S Highland
(74) *Attorney, Agent, or Firm* — Abbott Medical Optics Inc.

(57) ABSTRACT

A cap configured and dimensioned to sweep or fold one or more haptics when removed from an insertion device. The cap may further have a pin, one or more snaps and/or one or more locks. The cap may also have one or more ports and/or one or more windows. An insertion system having a handpiece, a cartridge, and a cap configured and dimensioned to sweep or fold one or more haptics when the cap is removed from the insertion system. The cap is configured and dimensioned to couple with the distal end of the cartridge.

19 Claims, 48 Drawing Sheets

Related U.S. Application Data filed on Mar. 25, 2011, provisional application No. 61/500,564, filed on Jun. 23, 2011.

(56) References Cited

U.S. PATENT DOCUMENTS

| | | | |
|---|---|---|---|
| 4,702,244 | A | 10/1987 | Mazzocco |
| 4,763,650 | A | 8/1988 | Hauser |
| 4,838,871 | A * | 6/1989 | Luther ................ A61M 5/3216 604/192 |
| 4,909,793 | A | 3/1990 | Vining et al. |
| 5,066,297 | A | 11/1991 | Cumming |
| 5,171,241 | A | 12/1992 | Buboltz et al. |
| 5,207,653 | A * | 5/1993 | Janjua ................ A61B 5/1405 604/192 |
| 5,275,604 | A | 1/1994 | Rheinish et al. |
| 5,304,182 | A * | 4/1994 | Rheinish ................ A61F 2/167 128/898 |
| 5,383,857 | A | 1/1995 | Levitov |
| 5,494,484 | A * | 2/1996 | Feingold ............... A61F 2/1678 206/5.1 |
| 5,496,328 | A | 3/1996 | Nakajima et al. |
| 5,499,987 | A | 3/1996 | Feingold |
| 5,578,042 | A | 11/1996 | Cumming |
| 5,616,148 | A | 4/1997 | Eagles et al. |
| 5,620,450 | A | 4/1997 | Eagles et al. |
| 5,630,841 | A | 5/1997 | McDonald |
| 5,728,102 | A | 3/1998 | Feingold et al. |
| 5,766,181 | A | 6/1998 | Chambers et al. |
| 5,772,666 | A | 6/1998 | Feingold et al. |
| 5,776,138 | A | 7/1998 | Vidal et al. |
| 5,800,442 | A | 9/1998 | Wolf et al. |
| 5,807,400 | A | 9/1998 | Chambers et al. |
| 5,860,984 | A | 1/1999 | Chambers et al. |
| 5,868,751 | A | 2/1999 | Feingold |
| 5,873,879 | A | 2/1999 | Figueroa et al. |
| 5,876,406 | A | 3/1999 | Wolf et al. |
| 5,876,440 | A | 3/1999 | Feingold |
| 5,891,152 | A | 4/1999 | Feingold |
| 5,902,307 | A | 5/1999 | Feingold et al. |
| 5,928,245 | A | 7/1999 | Wolf et al. |
| 5,941,886 | A | 8/1999 | Feingold |
| 5,942,277 | A | 8/1999 | Makker et al. |
| 5,947,975 | A | 9/1999 | Kikuchi et al. |
| 5,947,976 | A | 9/1999 | Van Noy et al. |
| 6,001,107 | A | 12/1999 | Feingold |
| 6,010,510 | A | 1/2000 | Brown et al. |
| 6,022,358 | A | 2/2000 | Wolf et al. |
| 6,048,347 | A | 4/2000 | Erdman |
| 6,048,348 | A | 4/2000 | Chambers et al. |
| 6,056,757 | A | 5/2000 | Feingold et al. |
| 6,059,791 | A | 5/2000 | Chambers |
| 6,129,733 | A | 10/2000 | Brady et al. |
| 6,143,001 | A | 11/2000 | Brown et al. |
| 6,203,549 | B1 | 3/2001 | Waldock |
| 6,228,094 | B1 | 5/2001 | Erdman |
| 6,283,976 | B1 | 9/2001 | Portney |
| 6,312,433 | B1 | 11/2001 | Butts et al. |
| 6,336,932 | B1 * | 1/2002 | Figueroa ................ A61F 2/167 606/107 |
| 6,371,960 | B2 | 4/2002 | Heyman et al. |
| 6,387,101 | B1 | 5/2002 | Butts et al. |
| 6,406,481 | B2 | 6/2002 | Feingold et al. |
| 6,468,282 | B2 | 10/2002 | Kikuchi et al. |
| 6,491,697 | B1 | 12/2002 | Clark et al. |
| 6,506,195 | B2 | 1/2003 | Chambers et al. |
| 6,537,283 | B2 | 3/2003 | Van Noy |
| 6,558,395 | B2 | 5/2003 | Hjertman et al. |
| 6,666,871 | B2 | 12/2003 | Kikuchi et al. |
| 6,723,104 | B2 | 4/2004 | Ott |
| 6,733,507 | B2 | 5/2004 | McNicholas et al. |
| 6,786,911 | B2 | 9/2004 | Mitomo et al. |
| 6,858,033 | B2 | 2/2005 | Kobayashi |
| 6,921,405 | B2 | 7/2005 | Feingold et al. |
| 7,014,641 | B2 | 3/2006 | Kobayashi et al. |
| 7,025,782 | B2 | 4/2006 | Kobayashi et al. |
| 7,037,312 | B2 | 5/2006 | Kikuchi et al. |
| 7,037,328 | B2 | 5/2006 | Vincent |
| 7,131,976 | B2 | 11/2006 | Kobayashi et al. |
| 7,156,854 | B2 | 1/2007 | Brown et al. |
| 7,229,449 | B2 | 6/2007 | Jeannin et al. |
| 7,276,071 | B2 | 10/2007 | Lin et al. |
| 7,303,582 | B2 | 12/2007 | Brady |
| 7,422,604 | B2 | 9/2008 | Vaquero et al. |
| 7,429,263 | B2 | 9/2008 | Vaquero et al. |
| 7,494,505 | B2 | 2/2009 | Kappelhof et al. |
| 8,273,122 | B2 | 9/2012 | Anderson |
| 8,435,289 | B2 | 5/2013 | Cole et al. |
| 8,685,088 | B2 | 4/2014 | Anderson |
| 2001/0007942 | A1 | 7/2001 | Kikuchi et al. |
| 2002/0156486 | A1 | 10/2002 | Nadel |
| 2002/0193805 | A1 | 12/2002 | Ott et al. |
| 2003/0045930 | A1 | 3/2003 | Nguyen |
| 2003/0187455 | A1 | 10/2003 | Kobayashi et al. |
| 2003/0212407 | A1 | 11/2003 | Kikuchi et al. |
| 2004/0199174 | A1 | 10/2004 | Herberger et al. |
| 2004/0238392 | A1 * | 12/2004 | Peterson ............... A61F 2/1678 206/438 |
| 2004/0243141 | A1 | 12/2004 | Brown et al. |
| 2005/0125000 | A1 | 6/2005 | Tourrette et al. |
| 2005/0154399 | A1 | 7/2005 | Weber et al. |
| 2006/0184181 | A1 | 8/2006 | Cole et al. |
| 2008/0033449 | A1 | 2/2008 | Cole et al. |
| 2008/0058830 | A1 | 3/2008 | Cole et al. |
| 2008/0065096 | A1 | 3/2008 | Kappelhof et al. |
| 2008/0097459 | A1 | 4/2008 | Kammerlander et al. |
| 2008/0114313 | A1 | 5/2008 | Gomez et al. |
| 2008/0114373 | A1 * | 5/2008 | Rathert ................ A61F 2/1691 606/107 |
| 2009/0036827 | A1 | 2/2009 | Cazzini |
| 2009/0318933 | A1 * | 12/2009 | Anderson ............. A61F 2/1664 606/107 |
| 2010/0106160 | A1 * | 4/2010 | Tsai ...................... A61F 2/167 606/107 |
| 2010/0217273 | A1 | 8/2010 | Someya et al. |
| 2010/0256652 | A1 | 10/2010 | Kobayashi et al. |
| 2012/0238962 | A1 * | 9/2012 | Chin ................... A61M 5/3216 604/198 |

FOREIGN PATENT DOCUMENTS

| | | |
|---|---|---|
| EP | 0270257 A1 | 6/1988 |
| EP | 0363213 A2 | 4/1990 |
| EP | 0677298 A1 | 10/1995 |
| EP | 722292 B1 | 7/2003 |
| EP | 743840 B1 | 7/2003 |
| EP | 1338254 A1 | 8/2003 |
| EP | 1502559 A1 | 2/2005 |
| EP | 1776980 A1 | 4/2007 |
| EP | 1800622 A1 | 6/2007 |
| EP | 1360944 B1 | 9/2007 |
| EP | 2161005 A1 | 3/2010 |
| EP | 1737393 B1 | 6/2010 |
| EP | 2123239 B1 | 3/2012 |
| GB | 2405344 A | 3/2005 |
| GB | 2414409 A | 11/2005 |
| JP | H10309294 A | 11/1998 |
| JP | 2007330783 A | 12/2007 |
| JP | 4707016 B2 | 6/2011 |
| WO | 9302727 A1 | 2/1993 |
| WO | 9524863 A1 | 9/1995 |
| WO | 9615743 A1 | 5/1996 |
| WO | 9937247 A1 | 7/1999 |
| WO | 0187187 A1 | 11/2001 |
| WO | 03024356 A2 | 3/2003 |
| WO | 2004105648 A1 | 12/2004 |
| WO | 2004105649 A1 | 12/2004 |
| WO | 2005020853 A2 | 3/2005 |
| WO | 2005030097 A1 | 4/2005 |
| WO | 2005070341 A1 | 8/2005 |
| WO | 2007044980 A2 | 4/2007 |

(56) References Cited

FOREIGN PATENT DOCUMENTS

WO 2008014260 A1 1/2008
WO 2008060869 A2 5/2008

OTHER PUBLICATIONS

International Search Report and Written Opinion, mailed Nov. 5, 2009, and International Preliminary Report on Patentability, mailed Jan. 5, 2011, for Application No. PCT/US2009/048305, 15 pages.
International Search Report for Application No. PCT/US2011/049028, mailed on Jul. 12, 2012, 14 pages.
International Search Report for Application No. PCT/US2011/049030, mailed on Jul. 12, 2012, 6 pages.
Partial International Search Report for Application No. PCT/US2011/049029, mailed on Nov. 29, 2011, 4 pages.
Partial International Search Report for Application No. PCT/US2011/049030, mailed on Nov. 29, 2011, 4 pages.

\* cited by examiner

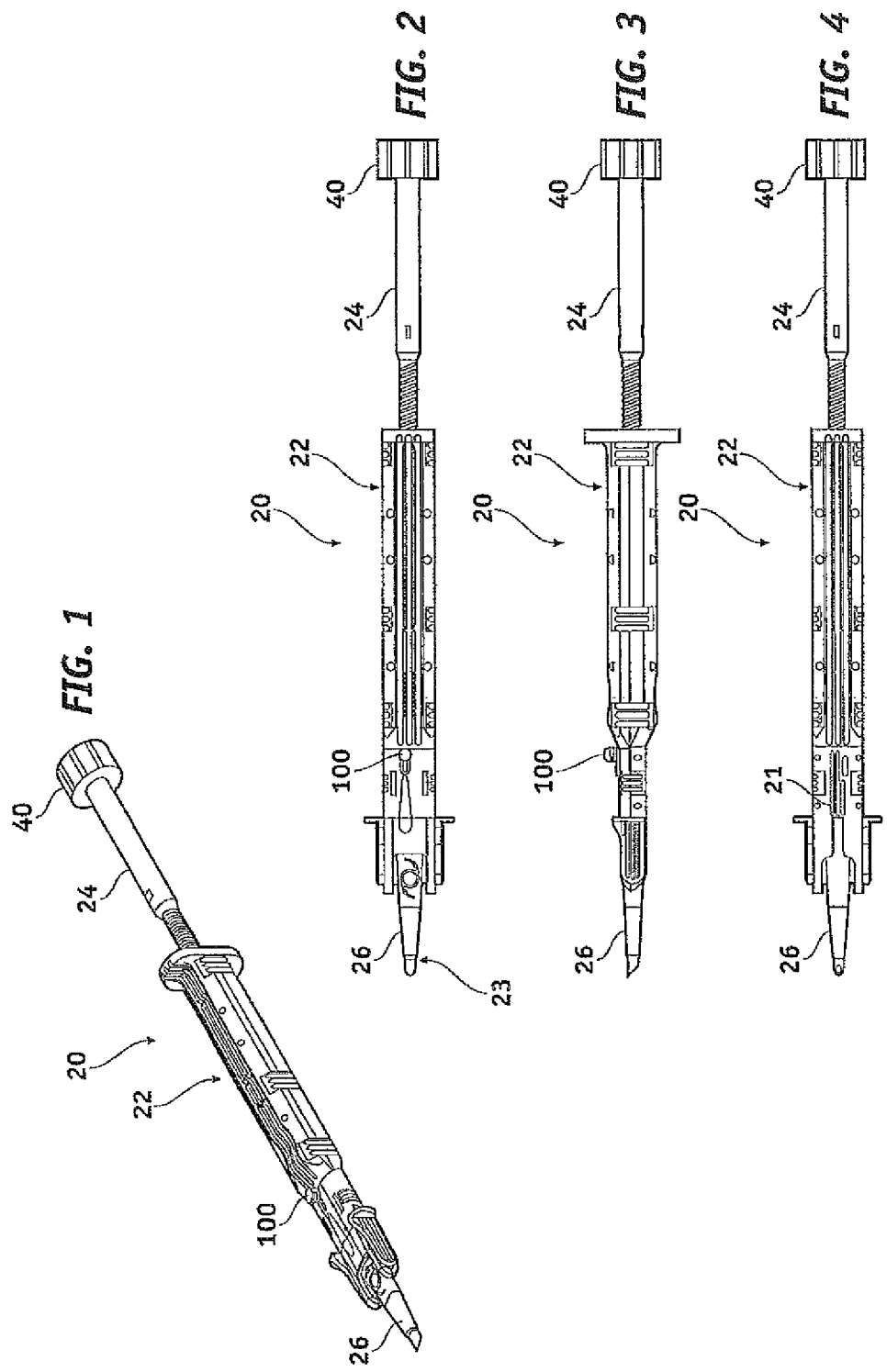

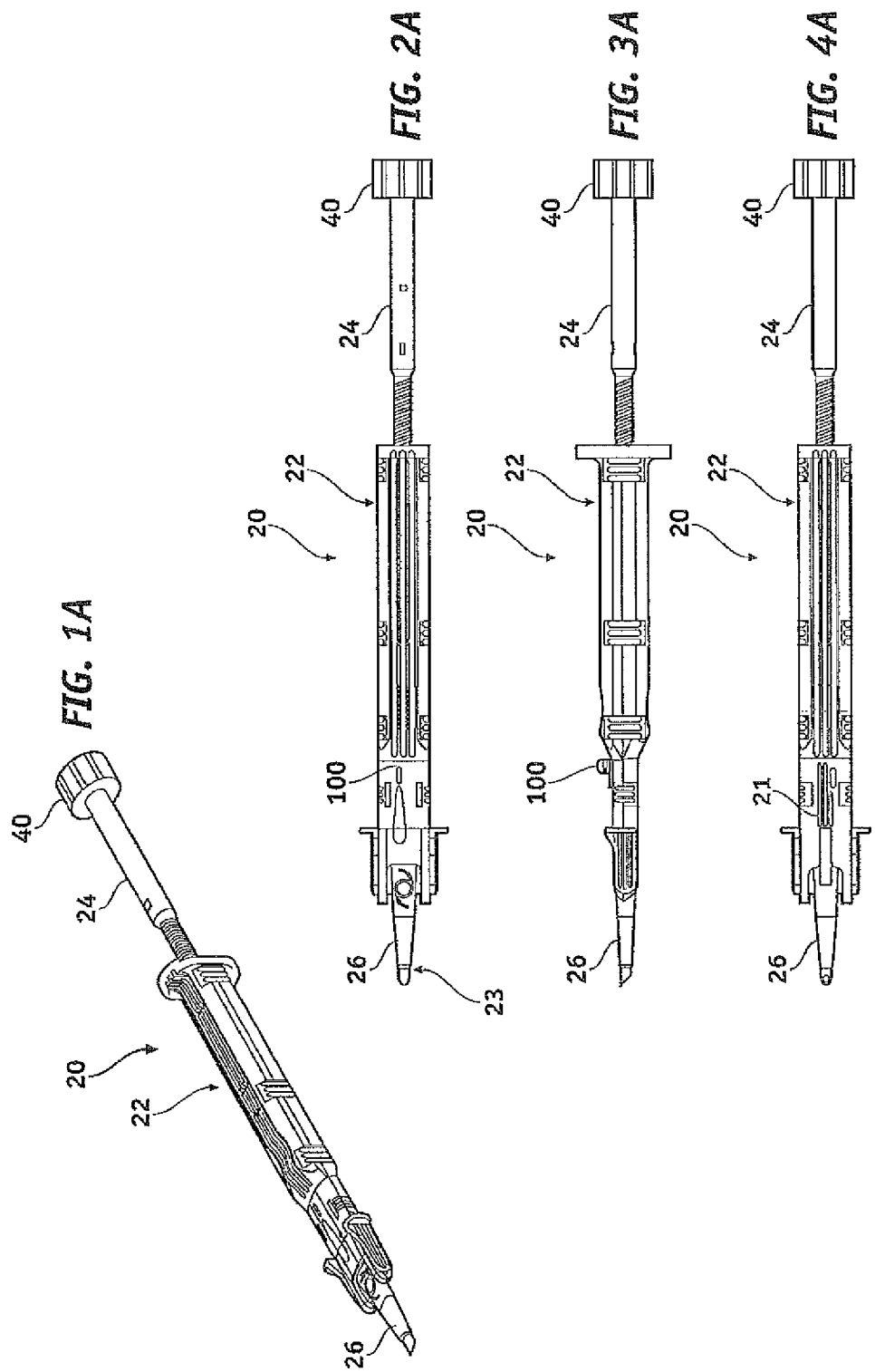

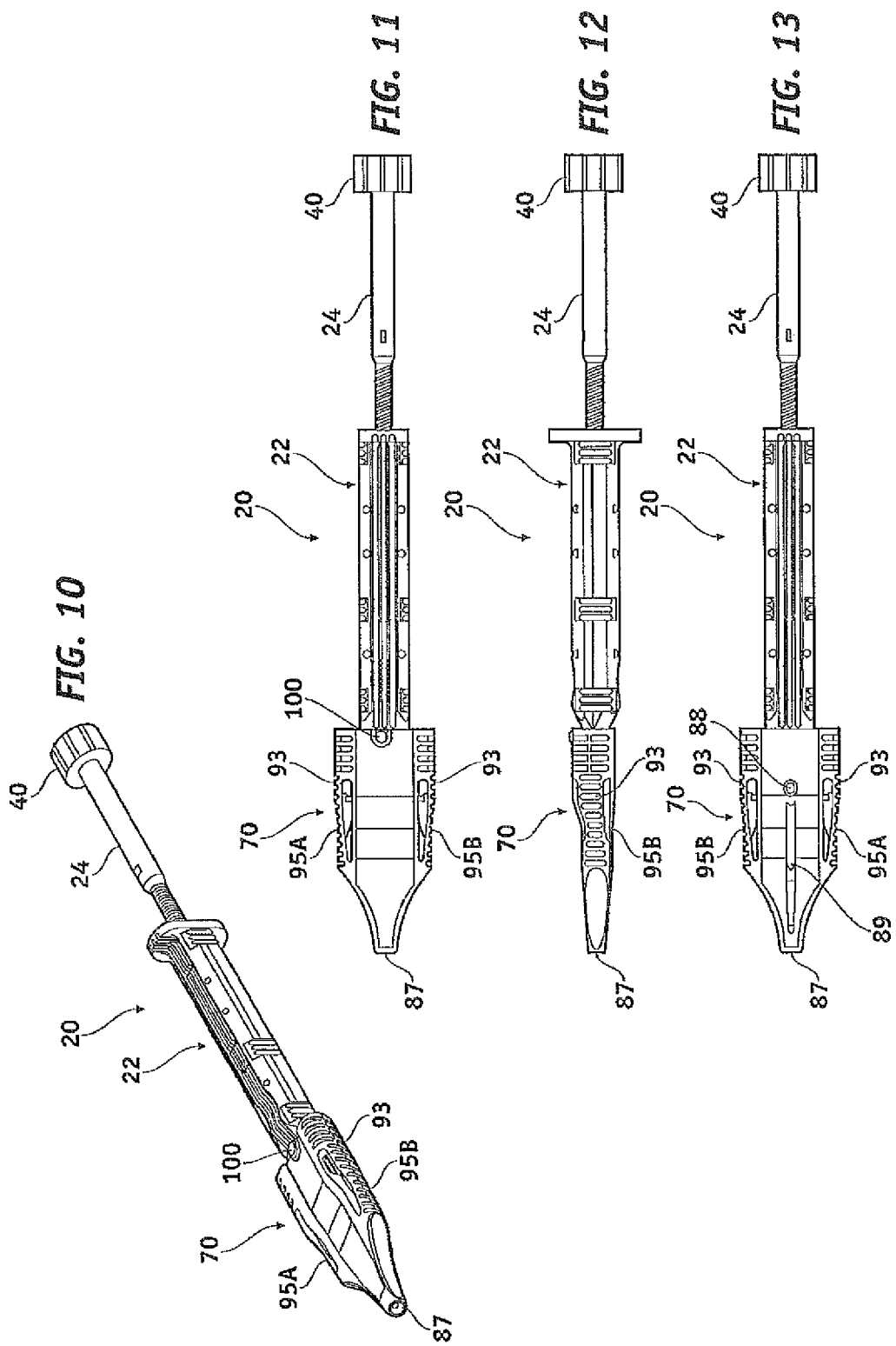

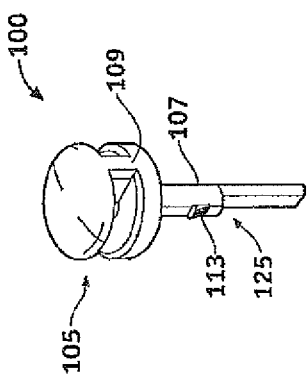
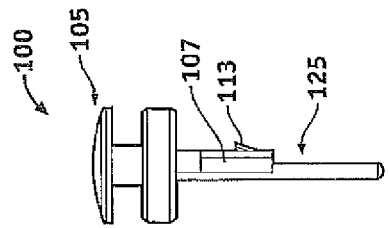
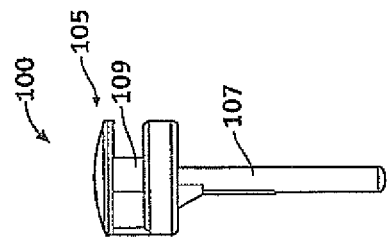
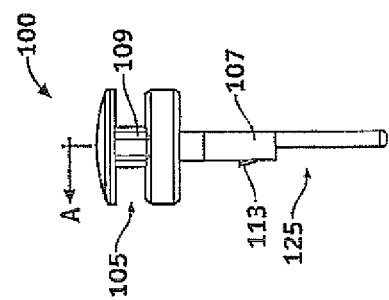
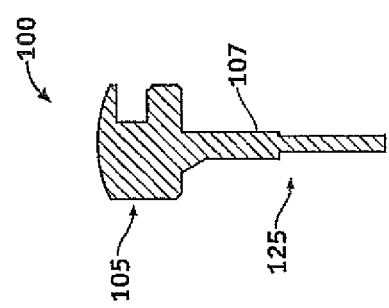

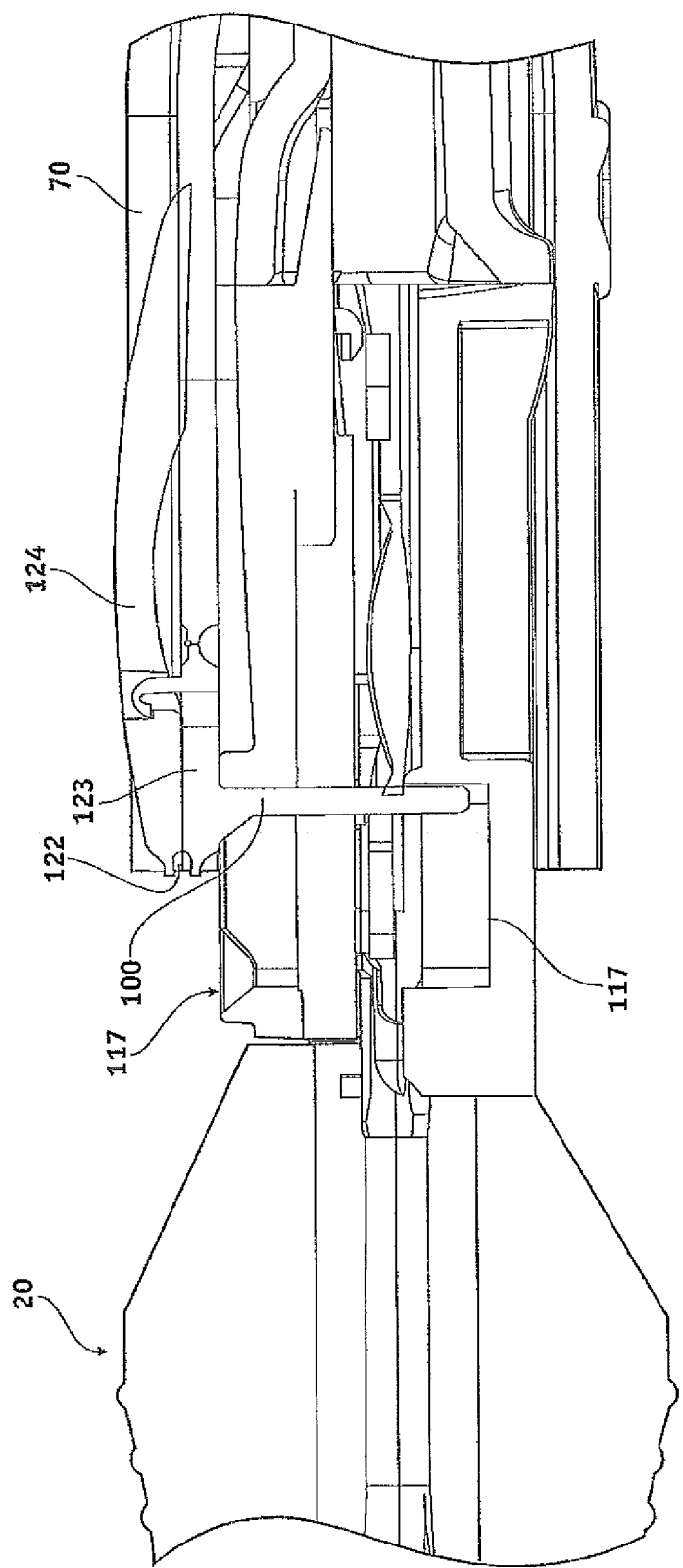

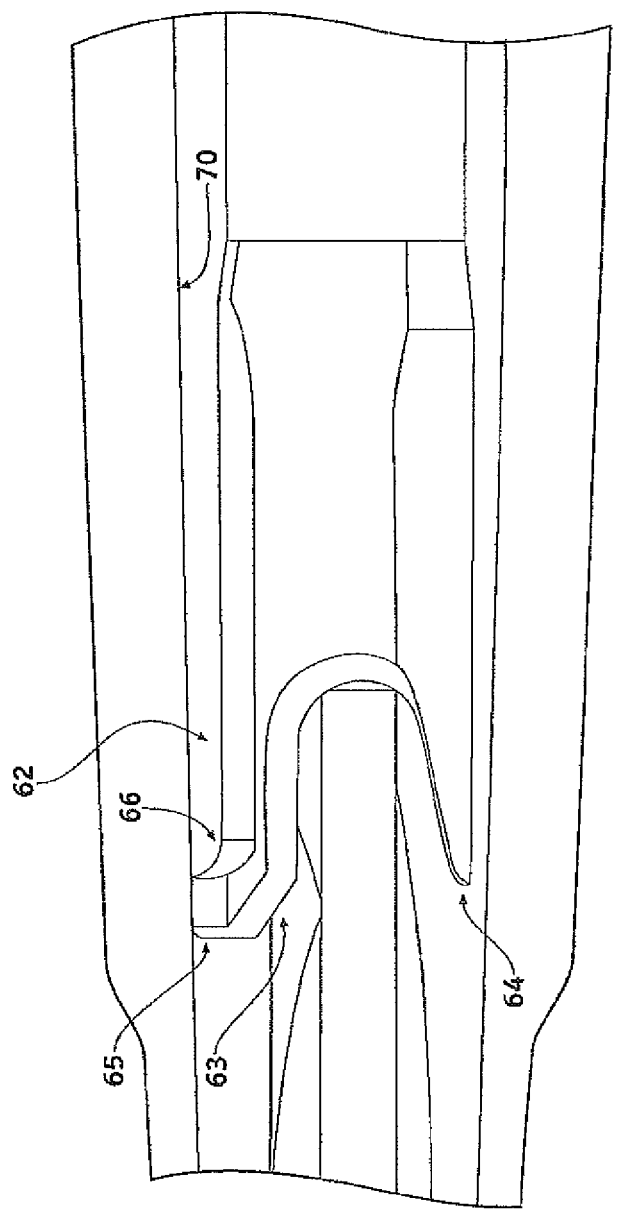

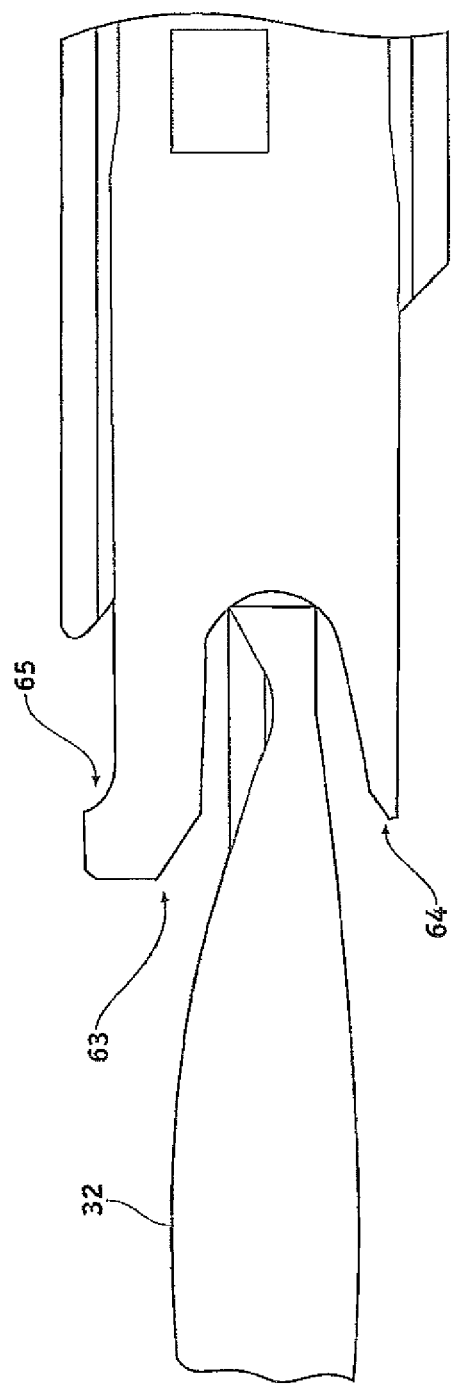

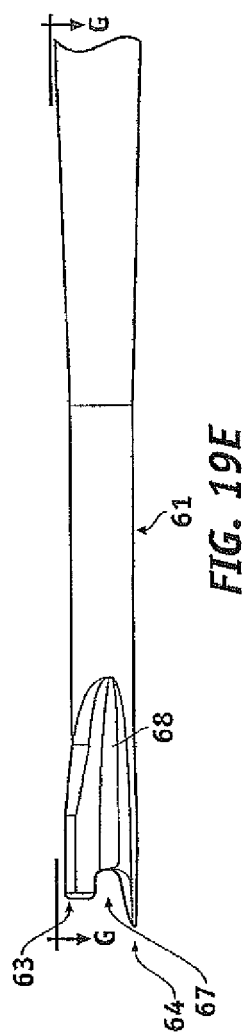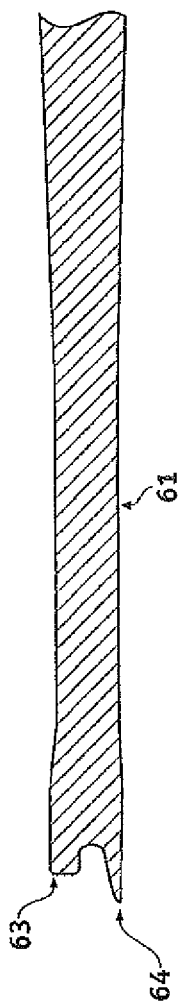

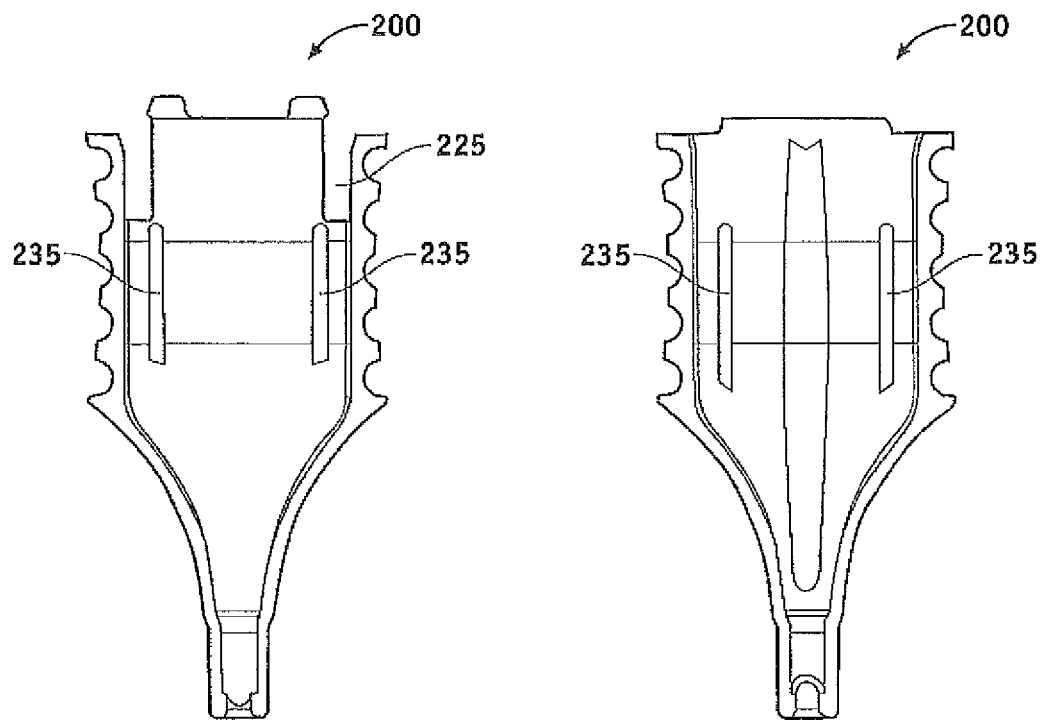
FIG. 23A
SECTION A-A
FIG. 23B
SECTION B-B
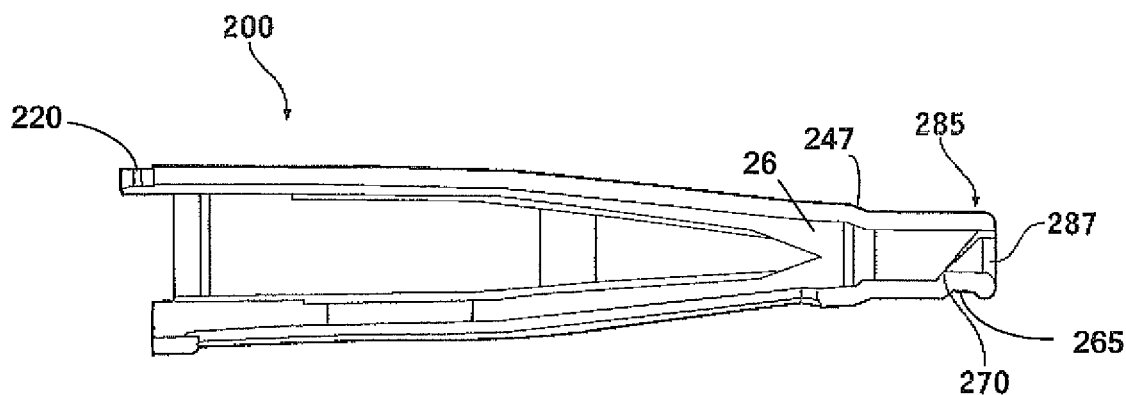
FIG. 24
SECTION C-C

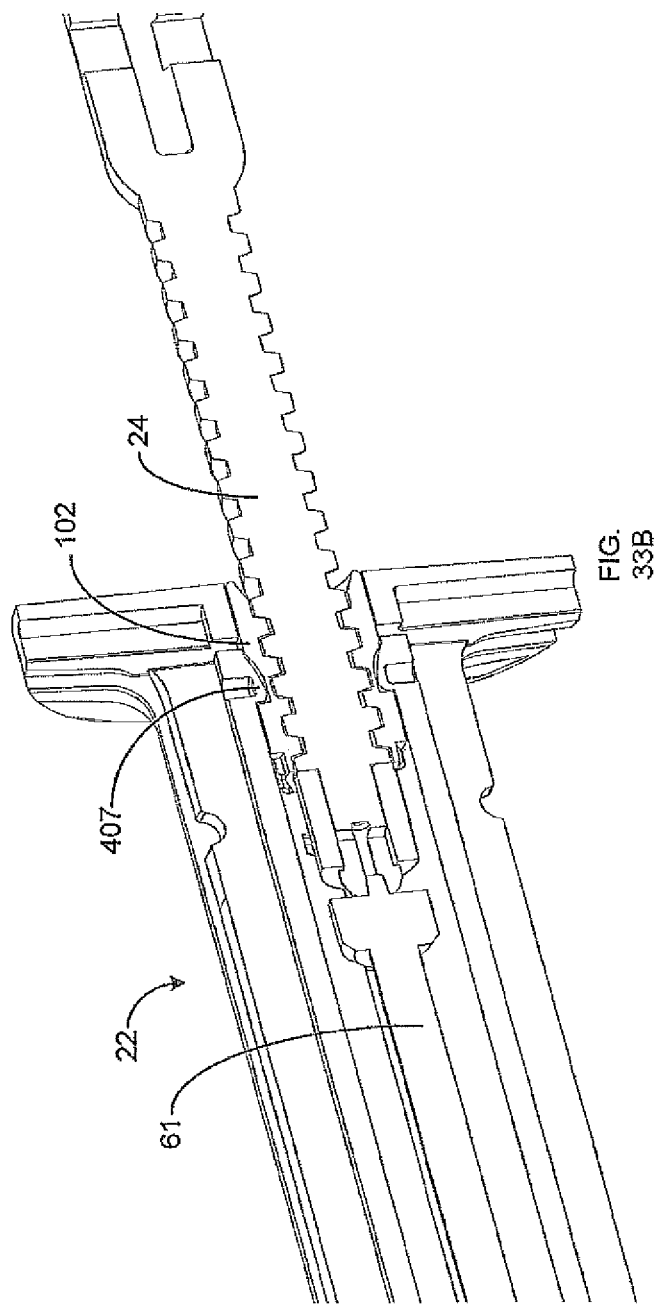

INSERTER CAP AND RELATED FEATURES

CROSS-REFERENCE TO RELATED PATENTS AND APPLICATIONS

This application claims priority to U.S. Provisional Application Nos. 61/376,661, filed on Aug. 24, 2010; 61/467,584, filed on Mar. 25, 2011; and 61/500,564, filed on Jun. 23, 2011, each of which is hereby incorporated by reference in its entirety.

TECHNICAL FIELD OF THE INVENTION

The present invention relates to an inserter cap and related features.

BACKGROUND OF THE INVENTION

It is estimated that 73% of Americans between the ages of 65 to 74 get cataracts. A cataract is a clouding of the eye's lens that impairs a person's vision and, if left untreated, causes blindness. As a result, each year approximately 1.4 million people in the United States alone undergo cataract surgery, whereby the clouded natural crystalline lens is removed and replaced with an intraocular lens (IOL) implant.

Surgeons implant IOLs not only as a replacement for the natural crystalline lens but also to alter the optical properties of (provide vision correction to) an eye with an existing IOL or in which the natural lens remains. IOLs often include an optically clear disk-like optic of about 6 mm in diameter, and preferably at least one flexible fixation member or haptic which extends radially outward from the optic and becomes affixed in the eye to secure the lens in position.

The optics may be constructed of rigid biocompatible materials such as polymethyl methacrylate (PMMA) or deformable materials such as silicone polymeric materials, acrylic polymeric materials, hydrogel polymeric materials, and the like. The deformable materials allow the IOL to be rolled or folded for insertion through an injector or insertion cartridge and an incision into the eye. Once within the chamber of the eye, the IOL is expulsed from the injector and returns to its original shape.

Injectors or inserters for delivering IOLs into the eye typically employ a handpiece and a removable cartridge that receives the IOL and has a hollow insertion tube or cannula through which the folded IOL is passed using a pushrod. Some inserters do without the cartridge. The inserter may be wholly or partly reusable, in which case the inserter or handpiece is usually made of some type of metal alloy that can be sterilized. Alternatively, disposable inserters made of less expensive materials, such as plastics, remain in a sterile package until ready for use. In some cases, the IOL is stored separately and transferred to a load chamber in the inserter or cartridge just prior to delivery. One particularly useful arrangement wherein the cartridge folds over an IOL is disclosed in U.S. Pat. No. 4,681,102 to Bartell. A cartridge opens to receive an IOL in a load chamber, and then folds closed and fits into an injector. A syringe-like plunger in the injector pushes the IOL from the load chamber through a tapered tube into the eye. The IOL unfolds as it emerges from the tip of the tapered tube. Another such insertion system is disclosed in Makker et al., U.S. Pat. No. 5,942,277. An example of storing an IOL in an inserter component is seen in U.S. Pat. No. 7,156,854, filed May 28, 2003. In the '854 patent, a nozzle portion 12 along with a removable stop 26 retains the IOL therein during storage and has internal ramps that assist in folding the IOL optic during an implant procedure. Also, U.S. Patent Publication No. 2008/0058830, filed Jul. 17, 2007, discloses a number of configurations for pre-loading IOLs for transfer to an insertion apparatus, and is expressly incorporated herein. Another preloaded insertion system is illustrated in U.S. Patent Publication No. 2009/0318933, filed Jun. 23, 2008, which is hereby incorporated by reference in its entirety.

Despite the advances in the area of insertion devices, there remains a need for devices and systems that increase the ease of use of inserters, including facilitating the insertion of IOLs, while reducing the risk of damage to both the insertion device and the IOL.

SUMMARY OF THE INVENTION

The present inventions disclose an insertion system, comprising a handpiece having a longitudinal axis, a distal end, and a proximal end, wherein the handpiece comprises a body; wherein the body comprises a slot near the distal end that is parallel to the longitudinal axis; a cartridge comprising a delivery tube at a distal end; wherein the cartridge is configured and dimensioned to couple with the distal end of the handpiece; a pin, wherein the pin is configured and dimensioned to couple with the slot and move along a distance within the slot; and a cap comprising a snap; wherein the cap is configured and dimensioned to couple with the distal end of the cartridge; and wherein the snap is configured and dimensioned to couple with the pin. In an embodiment, the pin may also comprise a top and stem, and the stem may couple with the slot and be configured and dimensioned to move within the slot. According to another embodiment, the snap may comprise a keyway, wherein the keyway is configured and dimensioned to couple with the pin. In an embodiment, the cap may also have one or more ports, one or more windows, and/or one or more locks located on different sides of the cap.

According to an embodiment, a cap for an insertion system comprises a body having a longitudinal axis, a distal end, and a proximal end; wherein the body comprises a snap at or near the proximal end, and wherein the snap is configured and dimensioned to couple with a pin. In an embodiment, the cap may also have one or more ports, which may be located at various locations, including at the distal end. In another embodiment, the cap may also have one or more windows and/or one or more snaps.

According to another embodiment, a cap comprises a body having a longitudinal axis, a distal end, and a proximal end; and a pin, wherein the pin is coupled with the body at or near the proximal end by one or more arms and one or more hinges.

According to another embodiment, a method for sweeping a haptic of an IOL comprises providing an insertion system, a cap, and a pin, wherein the insertion system comprises an IOL having a haptic, a cartridge comprising a delivery tube at a distal end and a handpiece having a longitudinal axis, a distal end, and a proximal end; wherein the handpiece comprises a body and the handpiece body comprises a slot near the distal end that is parallel to the longitudinal axis; and wherein the cartridge is configured and dimensioned to couple with the distal end of the handpiece; wherein the cap comprises a body having a longitudinal axis, a distal end, and a proximal end, and a locking mechanism, wherein the cap body comprises a snap at or near the proximal end, and wherein the snap is configured and dimensioned to couple with the pin; wherein the pin comprises a top and a stem and wherein the stem is configured and dimensioned to couple with the slot and is configured and dimensioned to move within the slot; wherein the cap is coupled with a distal end of the insertion system; deactivating the locking mechanism; advancing the cap in a distal direction to move the pin coupled with the cap along the slot from a first position to a second position; and removing the cap from the insertion system, thereby sweeping the haptic in a distal direction.

BRIEF DESCRIPTION OF THE DRAWINGS

The present invention is best understood with reference to the following detailed description of the invention and the drawings in which:

FIG. 1 is an assembled perspective view of an insertion system according to an embodiment of the invention;

FIG. 1A is an assembled perspective view of an insertion system according to an embodiment of the invention;

FIG. 2 is a top view of an insertion system according to an embodiment of the invention;

FIG. 2A is a top view of an insertion system according to an embodiment of the invention;

FIG. 3 is a side view of an insertion system according to an embodiment of the invention;

FIG. 3A is a side view of an insertion system according to an embodiment of the invention;

FIG. 4 is a bottom view of an insertion system according to an embodiment of the invention;

FIG. 4A is a bottom view of an insertion system according to an embodiment of the invention;

FIG. 10 is an assembled perspective view of an insertion system with a puller cap according to an embodiment of the invention;

FIG. 11 is an assembled perspective view of an insertion system with a puller cap according to an embodiment of the invention;

FIG. 12 is an assembled perspective view of an insertion system with a puller cap according to an embodiment of the invention;

FIG. 13 is an assembled perspective view of an insertion system with a puller cap according to an embodiment of the invention;

FIGS. 14A-E are multiple views of a pin according to an embodiment of the invention;

FIGS. 18A-C are cross-sectional views of an alternate embodiment of the puller cap;

FIG. 23A is a cross-sectional view of the protective cap shown in FIG. 22F;

FIG. 23B is a cross-sectional view of the protective cap shown in FIG. 22D;

FIG. 24A is a cross-sectional view of the protective cap shown in FIG. 22B;

FIG. 33B is a cross-sectional view of a nut lock according to an embodiment.

DETAILED DESCRIPTION OF THE INVENTION

Figure 5:
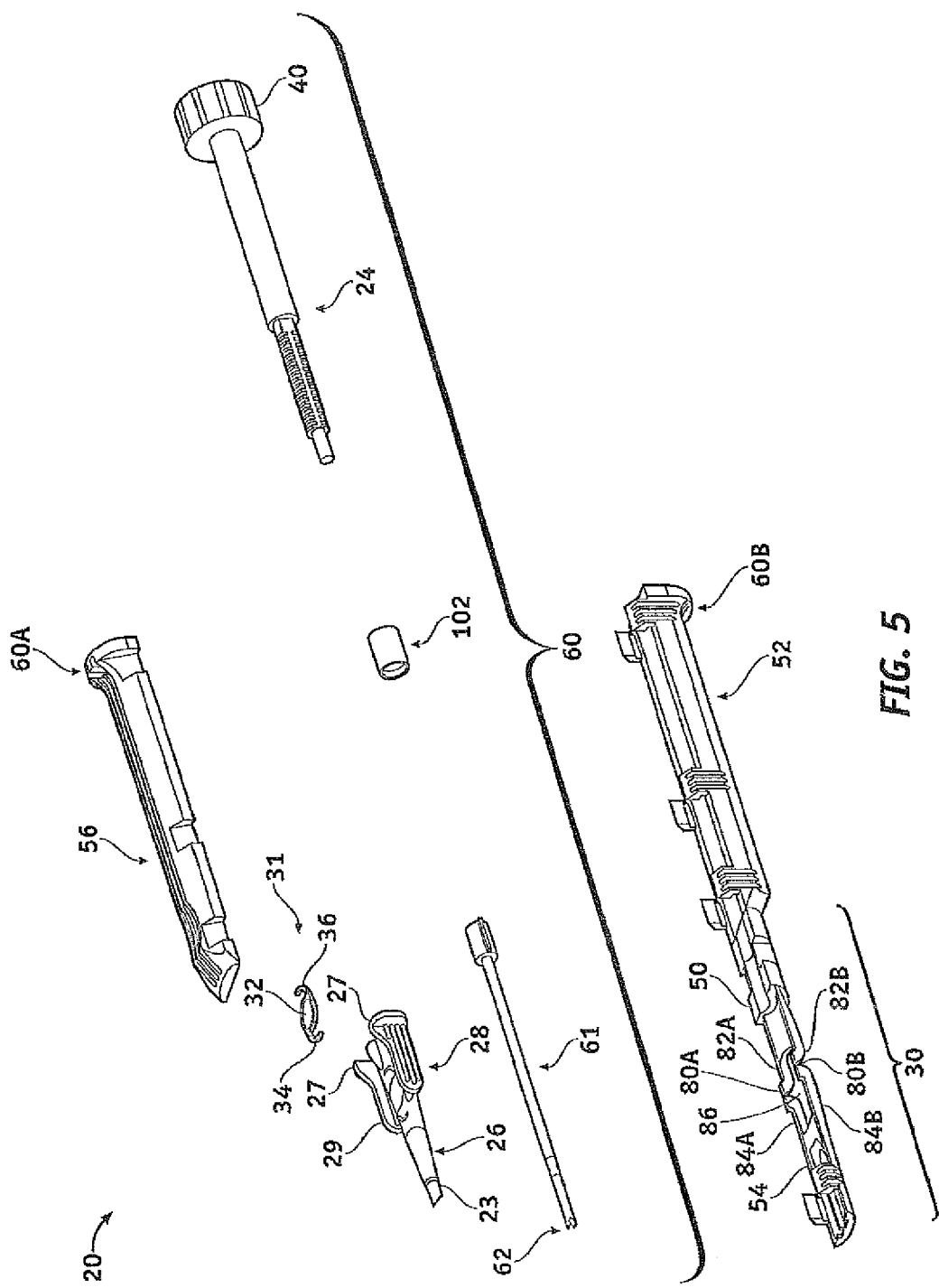
FIG. 5 is an exploded view of the insertion system according to FIGS. 1 and 1A.

Reference will now be made in detail to embodiments of the invention, examples of which are illustrated in the accompanying drawings. While the invention will be described in conjunction with the embodiments, it will be understood that they are not intended to limit the invention to those embodiments. On the contrary, the invention is intended to cover alternatives, modifications, and equivalents, which may be included within the spirit and scope of the invention as defined by the appended claims.

FIGS. 1-4 illustrate varying views of an exemplary IOL insertion system 20 of the present invention comprising a twist/syringe-style device having, generally, a handpiece 22, a plunger 24, and a delivery tube 26 on a distal end/portion thereof. As illustrated in FIGS. 1-3, IOL insertion system 20 may also include puller pin 100, which will be described in greater detail below. As illustrated in FIG. 4, system 20 also may comprise port 21 to enable application or insertion of a fluid, such as water, balance salt solution, and/or viscoelastic. FIGS. 1A-4A illustrates an alternative IOL insertion system 20 of the present invention. The IOL insertion system 20 illustrated in FIGS. 1A-4A does not include puller pin 100 or port 21. It is also envisioned that IOL insertion system 20 may include only one of the puller pin 100 or the port 21. The system 20 is also shown in an exploded view in FIG. 5.

IOL 31 is shown in FIG. 5 and may be positioned between two halves of a holding station 30. IOL 31 may comprise a central circular optic 32 having a leading haptic 34 and a trailing haptic 36 generally spirally extending therefrom. One exemplary IOL as illustrated is a one piece acrylic Tecnis® brand of aspheric IOL available from Abbott Medical Optics Inc. of Santa Ana, Calif. It is also envisioned that any IOL may be used with the insertion system disclosed herein.

With reference to FIGS. 1-5 and FIGS. 1A-4A, the system 20 defines a longitudinal axis from an end cap 40 of a pushrod assembly 60 at a proximal end to the delivery tube 26 at a distal end. The pushrod assembly 60 includes a plunger 24, an end cap 40, a nut lock 102, and a pushrod 61. Pushrod 61 may have a distal tip 62. In an embodiment, a portion of distal tip 62 may be flexible as described in greater detail below. In the illustrated embodiment, the distal tip 62 is forked to enable reliable capture of a proximal edge of the IOL optic 32 and/or trailing haptic 36. The plunger 24 and/or pushrod 61 translates axially through an elongate passage defined within the inserter handpiece 22 and is configured to urge the IOL from a holding station 30 through the distal delivery tube 26. In a general sense, the plunger 24 represents any actuator capable of displacing the IOL from the holding station 30 in a distal direction through a delivery tube or other such device. The plunger 24 therefore may be generally termed an actuator so as to encompass other prime movers that can perform the same function, such as a rotary actuators, threaded actuators, levers, etc.

FIG. 5 is an exploded view of the components of the system 20 in the orientation in which they will be assembled. However, a preferred mold configuration results in a total of six (or possibly fewer) components for the entire system, not counting the IOL. It is also envisioned that the mold configuration results in a total of seven or more components for the entire system, not counting the IOL depending upon many factors, including but not limited to manufacturing requirements. The six components shown in FIG. 5 include the plunger 24, the pushrod 61, the cartridge 28, the nut lock 102, the upper body 56, and the lower body 57. Lower body 57 may include the holding station 30 and base portion 52. Cartridge 28 comprises delivery tube 26 and wings 27. It is possible that the handpiece upper body 56 could be formed along with the remainder of the handpiece, though the mold would be fairly complicated and expensive. Likewise, the cartridge 28 could be incorporated into the handpiece 22, but again for reasons of manufacturing economy they are separate.

The one half of the holding station 30 comprises a base 50 that, in a preferred embodiment, forms a distal extension of a base portion 52 of the handpiece 22. The upper half of the holding station 30 comprises a cover 54 that abuts the upper body 56 of the inserter handpiece 22. In the illustrated embodiment, as seen in FIG. 5, the cover 54 and upper body 56 fit directly over the base 50 and base portion 52 to form the elongated handpiece 22. The overall shape of handpiece 22 may be of any shape to accommodate proper gripping of the device. According to an embodiment, the holding station cover 54 may be connected by a pair of living hinges 80a, 80b to the base 50. The base 50 includes a pair of bifurcated fingers 82a, 82b that meet a similar pair of bifurcated fingers 84a, 84b extending from the cover 54 at the living hinges 80a, 80b. The opposed pairs of aligned fingers 82, 84 are shaped so as to form slots therebetween when folded about the living hinges 80 and a central cavity 86 (shown in FIG. 5) for receiving a delivery tube 26, the combination of which is best seen in the assembled view of FIGS. 1 and 1A. In this regard, the delivery tube 26 desirably comprises a rear-loading cartridge as shown, and as described in co-pending U.S. Patent Publication No. 2009-0270876, filed on Apr. 28, 2008, which is hereby incorporated by reference in its entirety. In an embodiment, hinges 80a and 80b may be a snap feature instead of living hinges. In such an embodiment, holding station cover 54 may be molded as a separate part from base portion 52 and base 50.

The handpiece may further include a pair of proximal finger tabs 60a, 60b, one on the base portion 52 and one on the upper body 56. When an operator desires to depress the plunger 24, he or she places the thumb of one hand on the end cap 40, and index and middle fingers on respective finger tabs 60a, 60b. Squeezing the hand closed depresses the end cap 40 and moves the rest of pushrod assembly 60 along a lumen of the IOL insertion system 20 toward the distal end of the delivery tube 26.

Puller Cap

FIGS. 10-13 illustrate different views of system 20 with puller cap 70. Puller cap 70 fits over the holding station 30 and cartridge 28 in order to protect these components, and in particular the delivery tube 26, while also facilitating the insertion of fluid as further described below.

Figure 6:
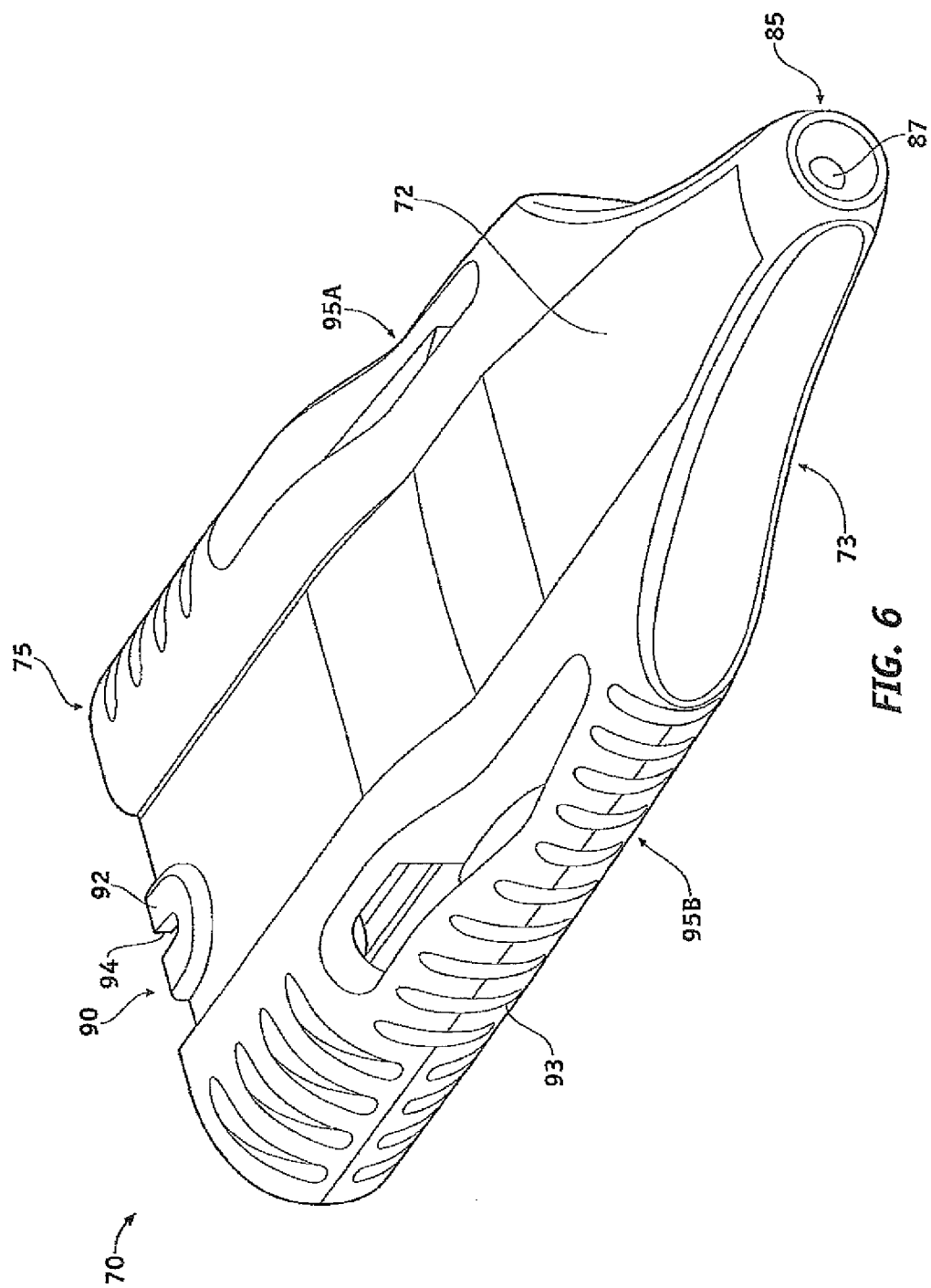
FIG. 6 is a perspective view of a puller cap according to an embodiment of the invention.
Figure 7:
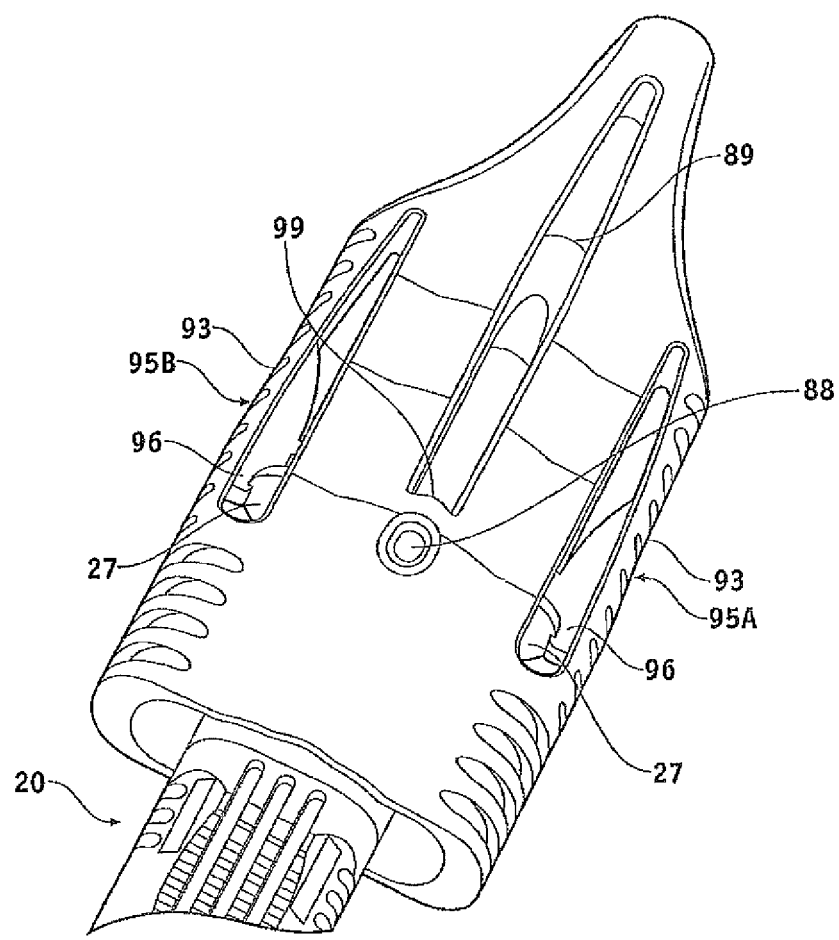
FIG. 7 is a perspective view of a puller cap according to an embodiment of the invention.

FIGS. 6 and 7 show two views of puller cap 70 of the present invention. In FIG. 6, puller cap 70 has a top 72, a bottom 73, a proximal end 75, and a distal end 85. Puller cap 70 includes lock 95A, 95B, grips 93, snap 90, and port 87. Puller cap 70 may be made of any material known in the art, but preferably polypropylene, polycarbonate, polyethylene, or polyethylene terephthalate; more preferably polypropylene and polycarbonate; most preferably polypropylene. Puller cap 70 may also be of any color, preferably translucent or clear to enable a user to visualize the features inside puller cap 70 and anything housed within puller cap 70. Puller cap 70 may be the shape as illustrated in the embodiment in FIG. 6, but the invention also envisions that puller cap 70 may be of any shape or size to accommodate the needs of the insertion system the puller cap is used with or the needs of the user the puller cap is designed for. For example, the puller cap may be of an arrow shape as illustrated in the embodiment in FIG. 6, may be more of a round shape, triangular shape, square shape, or shaped to meet the needs for shipping and/or handling. The puller cap may also include one or more hook features (not shown) to aid in the removal of the puller cap from an inserter. The hook feature may be located on any location on the puller cap, including but not limited to the top, bottom, on or near the snap, or near the distal or proximal ends. The hook feature may be of any shape or size to accommodate for the shape or size of the puller cap and may be of any shape or size to accommodate the fingers of a user.

The lock 95A and 95B may be of any design or configuration known in the art. According to an embodiment of the present invention, a portion 96 of locks 95A, 95B are configured and dimensioned to cam outwardly when external pressure is placed on the snaps in a perpendicular plane with respect to the longitudinal plane of system 20 from proximal end 75 to distal end 85. (See FIG. 7). Locks 95A, 95B may comprise a texture design or feature to ease gripping and/or actuation of the snaps and removal of puller cap 70 from an insertion system, such as insertion system 20 as illustrated in FIGS. 1-5 and 1A-4A. In an embodiment, puller cap 70 may have one or more grips having a texture design or feature and the lock 95A and 95B are separated from the one or more grips, such that squeezing of the grips does not deactivate locks 95A and 95B.

Figure 15:
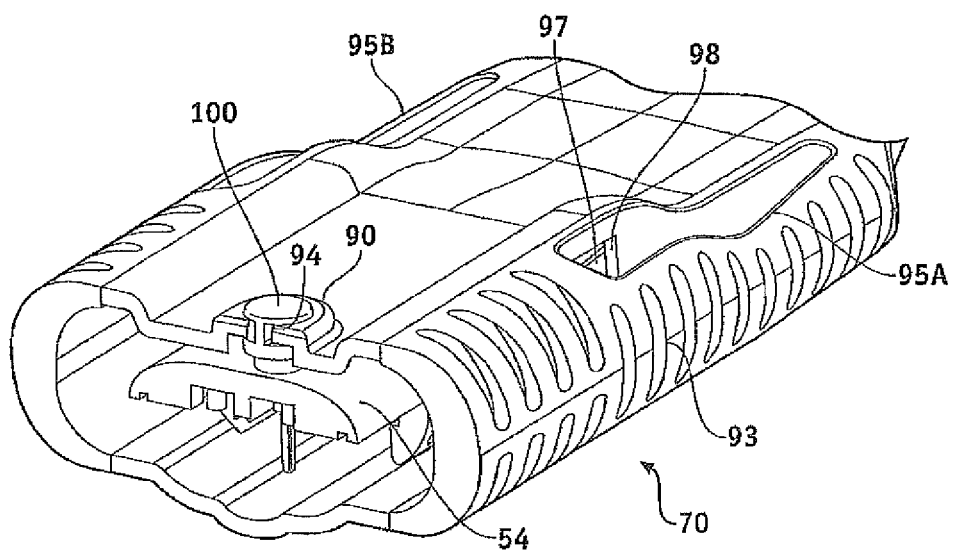
FIG. 15 is a cross-sectional perspective view of a puller cap and insertion system according to an embodiment of the invention.

As shown in FIG. 6, the snap 90 is designed and configured to couple with pin 100 (see FIGS. 14 and 15). Snap 90 may be of any shape or size as long as it is configured and dimensioned to mate with pin 100. According to the embodiment in FIG. 6, snap 90 comprises a canopy 92 and a keyway 94. In another embodiment, snap 90 does not have a canopy and only has keyway 94.

Puller cap 70 may include one or more ports 87 to aid in the insertion of a fluid, including but not limited to balanced salt solution, water, and/or viscoelastic. The one or more ports 87 mate with ports located on the insertion system 20 to assist with filling a portion of the system with fluid to provide lubrication to the internal features of the insertion system to aid in delivery of the IOL. With respect to port 87 as illustrated in FIG. 6, port 87 acts a funnel mechanism into the distal end of delivery tube 26. FIG. 7 illustrates a bottom view of puller cap 70 comprising port 88 and a window 89. The puller cap may also comprise one or more windows to provide the users with a visual indicator of the amount of fluid inserted into a portion of the insertion system, as well as provide viewing of the distal end of a cannula tip, which is typically used to inject a fluid. In an embodiment, the one or more windows may be located on the top, bottom or sides of the puller cap, preferably on the top or the bottom. The one or more windows may also comprise a measuring devise such as a ruler to allow a user to measure or see the amount of fluid inserted into the inserter. The window 89 may also have a fill indicator 99 such that a user fills a portion of the insertion system until the fluid reaches fill indicator 99 indicating a proper and/or maximum fill has been reached. The one or more windows may also comprise a material such that when a fluid is inserted into the insertion system and viewed through the window light that is emitted through the window to the fluid is polarized providing a visual indicator of the fluid within the inserter.

Figure 8:
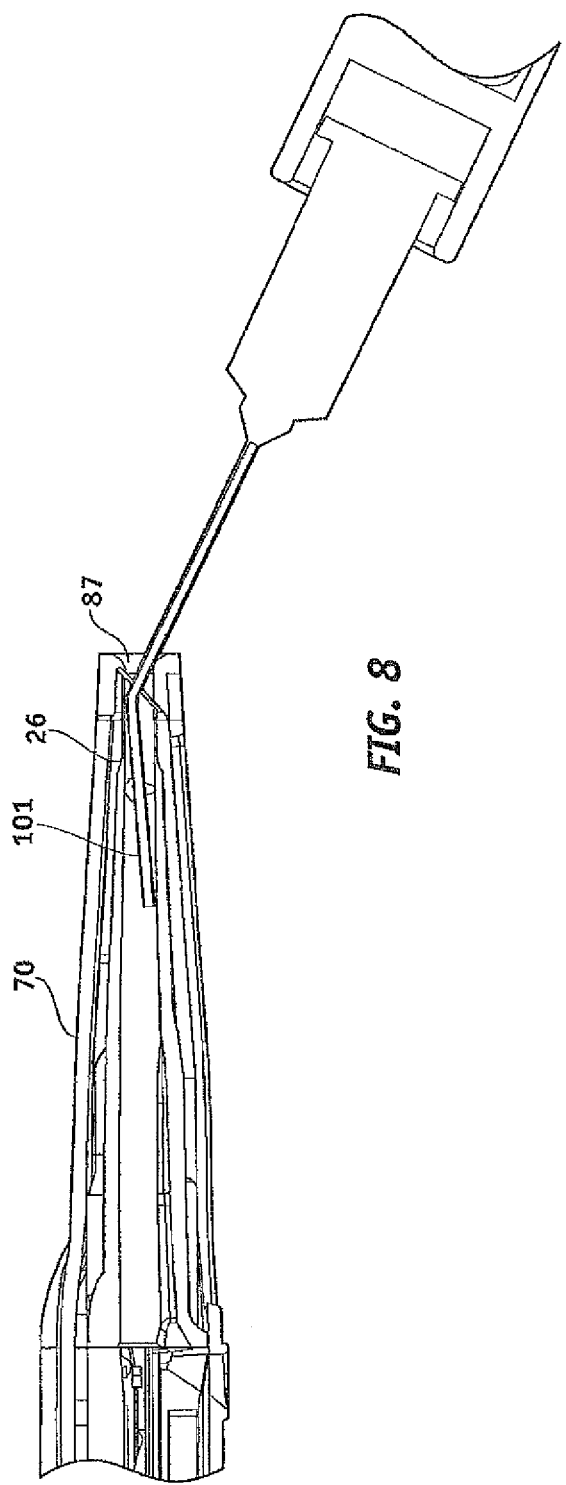
FIG. 8 is cross-sectional view of a puller cap and insertion system according to an embodiment of the invention.
Figure 9:
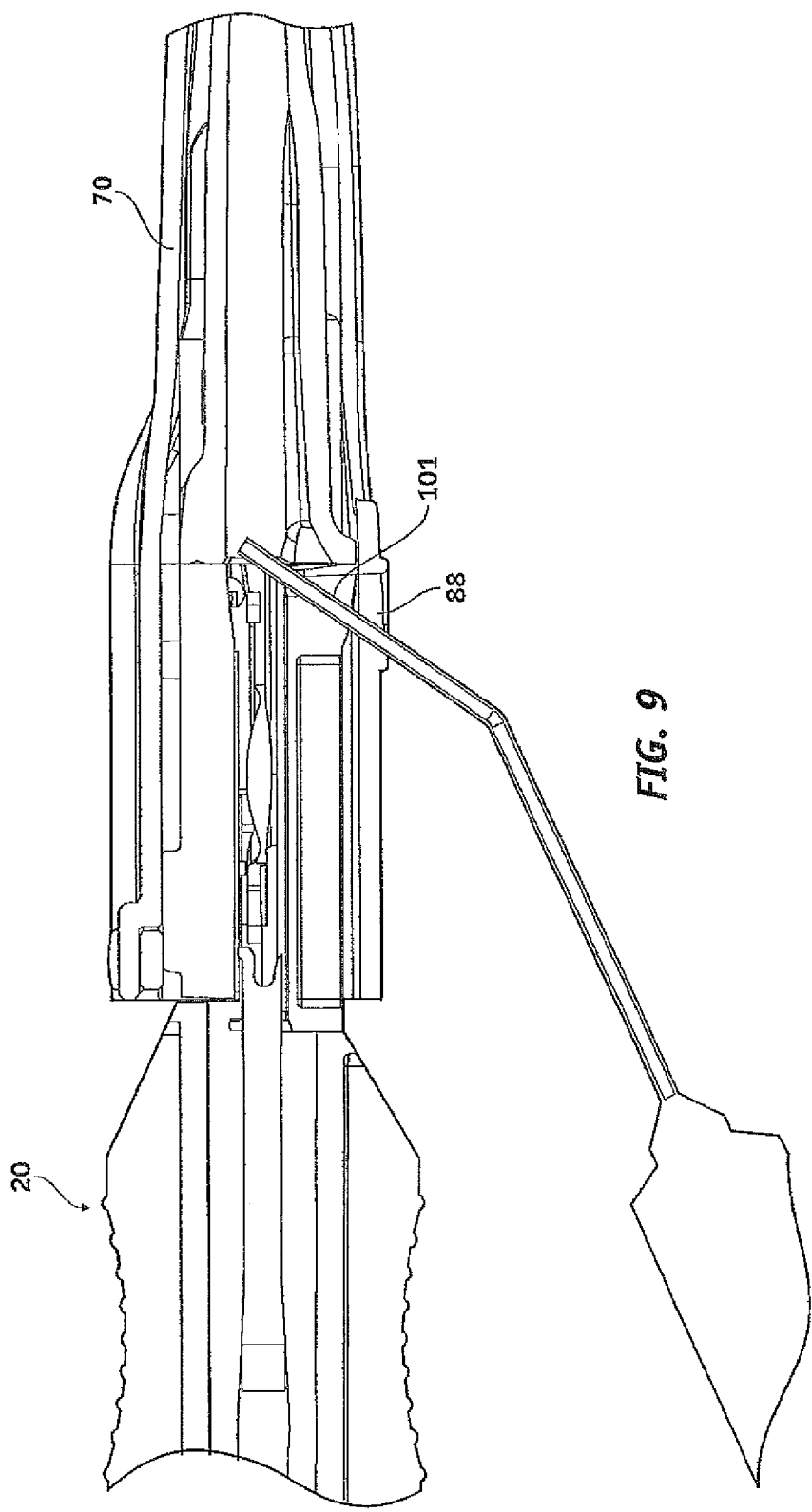
FIG. 9 is cross-sectional view of a puller cap and insertion system according to an embodiment of the invention.

As is well known in the art, the small nature of the ports of insertion systems known in the art can make it very difficult for doctors, nurses, and/or staff to locate openings for inserting fluids. The puller cap of the present invention solves this problem by providing a larger port with a funnel feature that leads into the smaller ports of the insertion system. This enables a user to more easily direct a cannula tip 101 into a delivery tube 26 or ports 87, 88 as illustrated in FIGS. 8 and 9.

Pin and Haptic Sweep Slot

FIGS. 14A-E shows pin 100 which includes top 105, stem 107, key 109, and lock 113. Top 105 comprises key 109 that may be of any shape or configuration so as to mate with snap 90. Lock 113 may be of any shape or size and is configured to mate with grove 115 of haptic sweep slot 117 of cover 54 (see FIG. 16). Lock 113 may also be located anywhere along stem 107 and the present invention also envisions more than one lock feature. Haptic sweep slot 117 may also be of any shape or size as long as it is configured to mate with pin 100. According to an embodiment, haptic sweep slot 117 runs along the same longitudinal axis of system 20. In an embodiment, the length of the haptic sweep slot is longer in length than the width the slot. In an embodiment, the length of the haptic sweep slot is between about 0.150 inches (in.) (3.81 millimeters (mm)) to about 0.170 in. (4.318 mm), preferably about 0.153 in. (3.8862 mm), more preferably about 0.165 in. (4.191 mm). In an embodiment, the width of the haptic sweep slot is about 0.028 in. (0.7112 mm) to about 0.040 in. (1.016 mm), preferably about 0.030 in. (0.762 mm), more preferably about 0.035 in. (0.889 mm). Pin 100 is configured and dimensioned to be inserted into haptic sweep slot 117 such that lock 113 and groove 115 are coupled together securing the two parts together, but still enabling the pin 100 to move within haptic sweep slot 117. Groove 115 may also be of any shape or size as long as it is configured to mate with lock 113. In an embodiment, there may be more than one groove in the haptic sweep slot. Groove 115 enables pin 100 to maintain a substantially perpendicular orientation with respect to the longitudinal axis of system 20. According to an embodiment, the substantially perpendicular orientation assists with sweeping or folding of trailing haptic 36 as further described below.

Pin 100 may comprise leg feature 125 (see FIG. 14A-14E); such that pushrod 61 is capable of passing step 107 once pin 100 has been advanced forward to sweep trailing haptic 36. The leg feature 125 results in stem 107 having a cut out or offset portion as shown in FIGS. 14A, B, C and E. To ensure that this leg feature 125 is in the correct orientation during manufacture, lock 109 may comprise a one-way directional snap feature or poke-oke as illustrated in an embodiment in FIGS. 14C and D.

In an embodiment, pin 100 is configured and dimensioned to penetrate or extend through cover 54 and base 50 or another portion of system 20 or similar device to sweep or fold a trailing or leading haptic or similar feature of an IOL.

Puller Cap and Pin Function

Figure 15A:
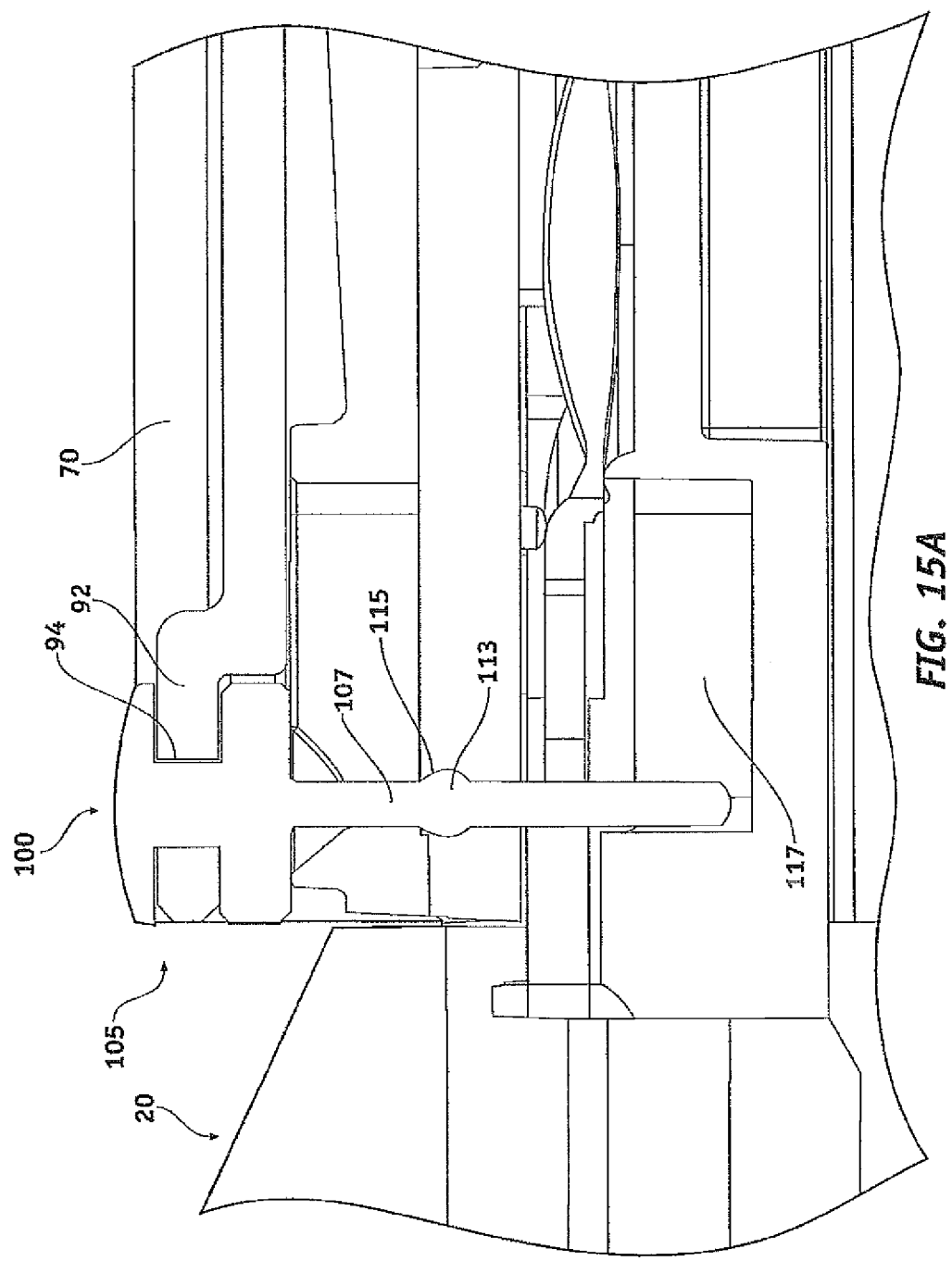
FIG. 15A is a cross-sectional view of a pin, puller cap, and insertion system according to an embodiment of the invention.
Figure 16:
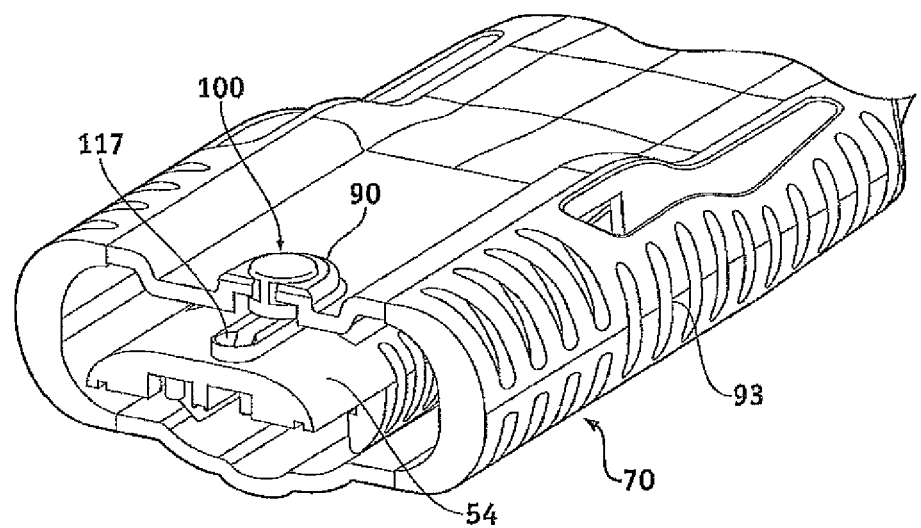
FIG. 16 is a cross-sectional perspective view of a puller cap and insertion system according to an embodiment of the invention.
Figure 17:
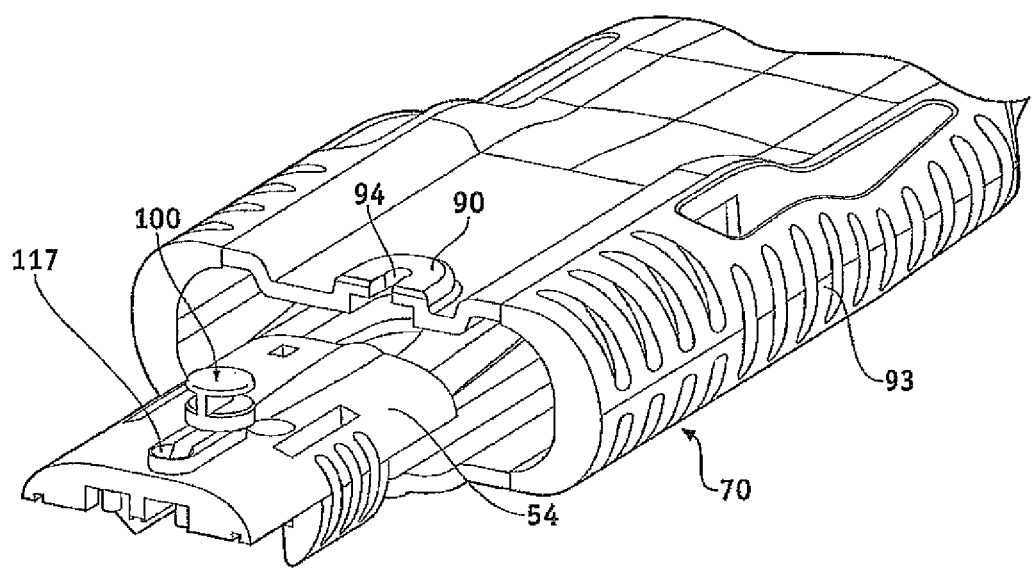
FIG. 17 is a cross-sectional perspective view of a puller cap and insertion system according to an embodiment of the invention.

As shown in FIGS. 10 and 15, as puller cap 70 is placed on system 20 to cover cartridge 28 and delivery tube 26, snap 90 mates or couples with pin 100 via key 109 and keyway 94. See FIG. 15A for a cross-sectional view showing pin 100 coupled with snap 92 in keyway 94 and lock 113 coupled with groove 115. In addition to the functions described above, puller cap 70 with pin 100 function to fold or sweep the trailing haptic 36 in the distal direction prior to folding or moving the IOL in the distal direction to insert the IOL into the eye. Folding or sweeping trailing haptic 36 in the distal direction controls the location of the haptic and prevents damage to the haptic during delivery of the IOL. Pin 100 may also sweep the trailing haptic 36 over a portion of optic 32 such that during movement of the IOL down the lumen of tube 26 at least a portion of the trailing haptic 36 is captured in the fold or folds of the optic 32. Prior to the present invention a user would have to manually use the distal end of a cannula to fold or sweep the trailing haptic, which was difficult to do due to the small nature of the slot. Moreover, it was difficult to visualize whether the haptic was in fact in place once the cannula moved the haptic. The present invention overcomes these problems. Once puller cap 70 is coupled with pin 100 a user may use the easy to access one or more ports 87, 88 to insert/inject fluid into system 20. Next, to sweep trailing haptic 36 a user may grasp and squeeze locks 95A, 95B to release the internal lock features, e.g. portion 96 of lock 95A, B from wings 27. As puller cap 70 is advanced distally from system 20 along the longitudinal axis of system 20 pin 100 slides along haptic sweep slot 117 and lock 113 slides in groove 115 as shown in FIG. 16. When pin 100 reaches the end of haptic sweep slot 117, pin 100 will release from snap 90, releasing puller cap 70 from system 20 as shown in FIG. 17. At this point, trailing haptic 36 has been swept or folded into the proper position without the use of another tool and the IOL is now ready for insertion into the eye.

Figure 18A:
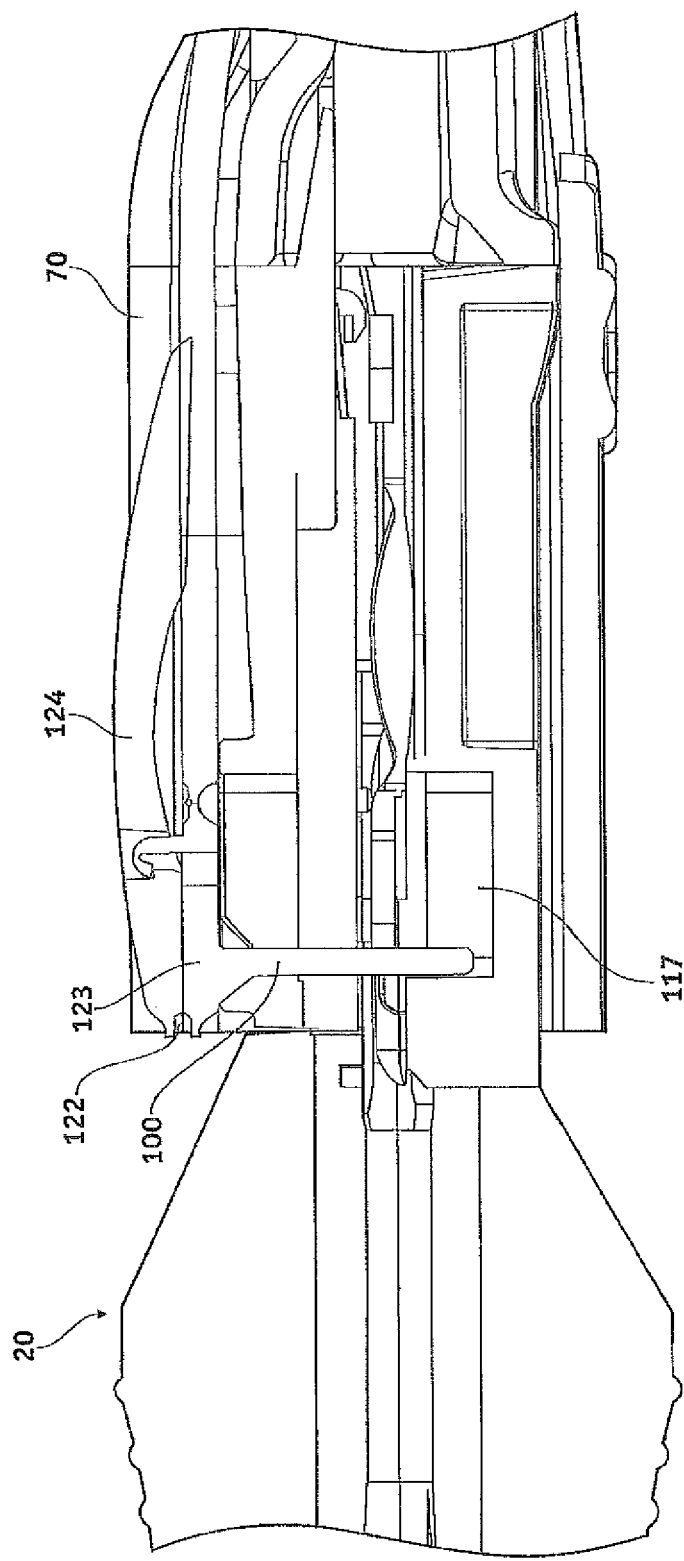
Figure 18C:
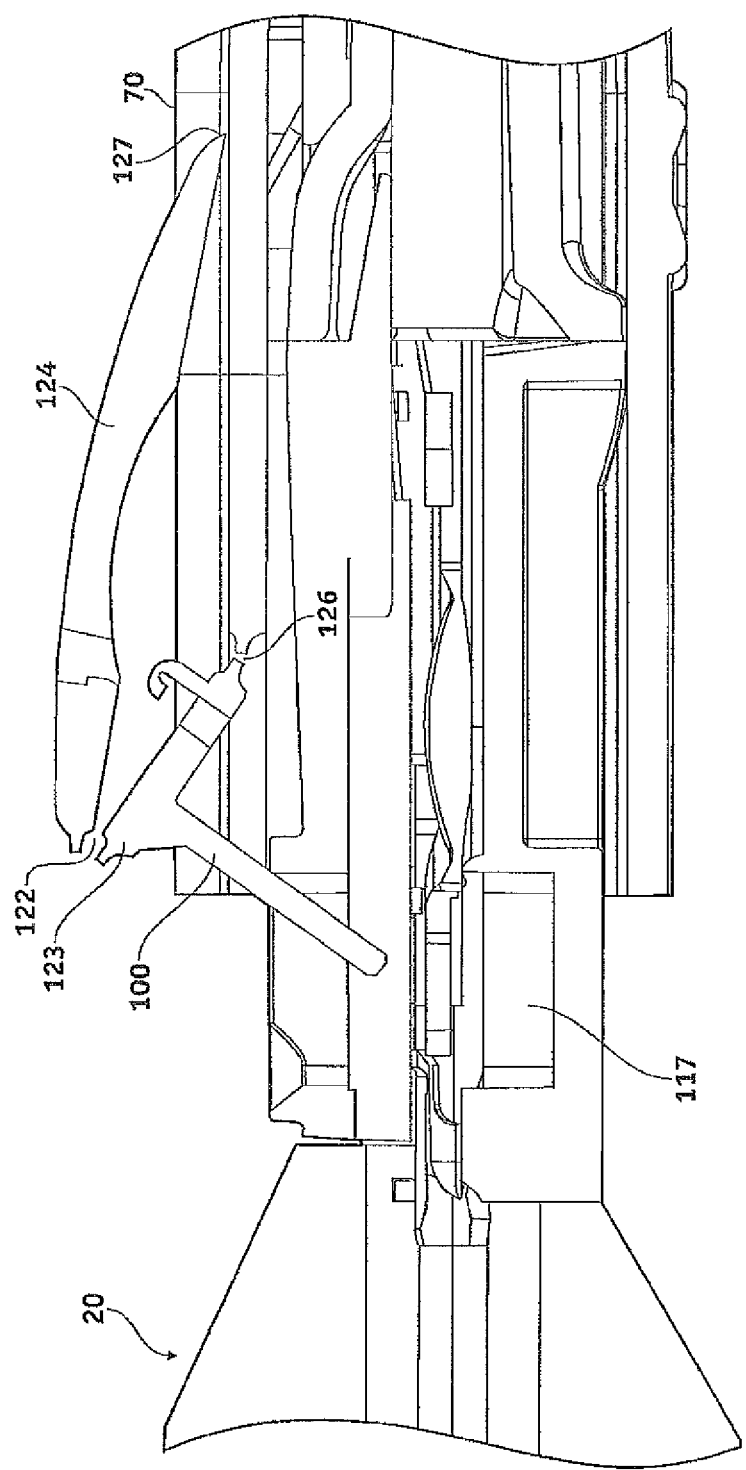
Figure 18D:
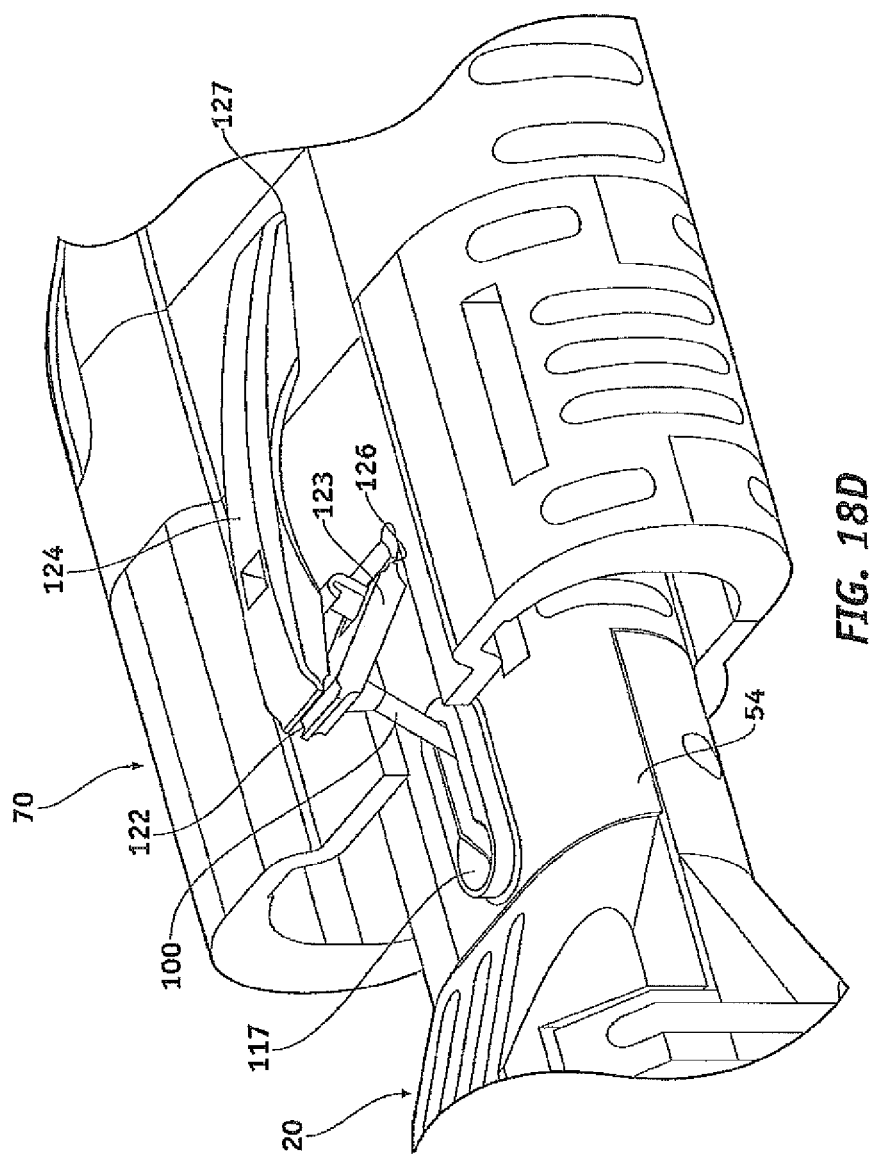
FIG. 18D is a perspective view of the alternative embodiment of the puller cap shown in FIGS. 18A-C.

In an alternate embodiment, pin 100 may release from cover 54 with puller cap 70. It is also envisioned that pin 100 may be connected to one or more arms and one or more hinges to aid in its connection to puller cap 70 and its release from system 20. FIG. 18A shows such an alternate embodiment of the present invention. In FIGS. 18A-D, pin 100 is connected to arm 123 which is connected to arm 124 via hinge 122. Arms 123 and 124 may further be coupled with puller cap 70 with hinge 126 and 127 (as shown in FIGS. 18C and 18D) or by any other mechanism known in the art. As puller cap 70 is moved distally along the longitudinal axis of system 20 to sweep trailing haptic 36 pin 100 is advanced along haptic sweep slot 117. When pin 100 reaches the end of haptic sweep slot 117, further advancement of puller cap 70 causes arm 124 to lift up thereby lifting arm 123 and lifting pin 100 from haptic sweep slot 117 and releasing puller cap 70 from system 20. In an embodiment, haptic sweep slot 117 may comprise a ramp at one or both ends of the slot. In particular, a haptic sweep slot 117 may comprise a ramp at the distal end 121 of the slot to aid in the release of pin 100 and/or puller cap 70 after trailing haptic 36 has been swept or folded. According to another embodiment, only a single arm or a single hinge may be used with pin 100. In another embodiment, one or more arms or one or more hinges may used with pin 100.

In an embodiment, pin 100 maintains trailing haptic 36 in the proper orientation for delivery and even if a user decides to place puller cap 70 back onto system 20, the internal features of system 20 still maintain trailing haptic 36 in the proper orientation. This allows a user to determine when she would like to use and/or the order in which she will use the haptic sweep feature, the port features, and the tip protection feature, which will be described further below.

Pushrod

Figure 19A:
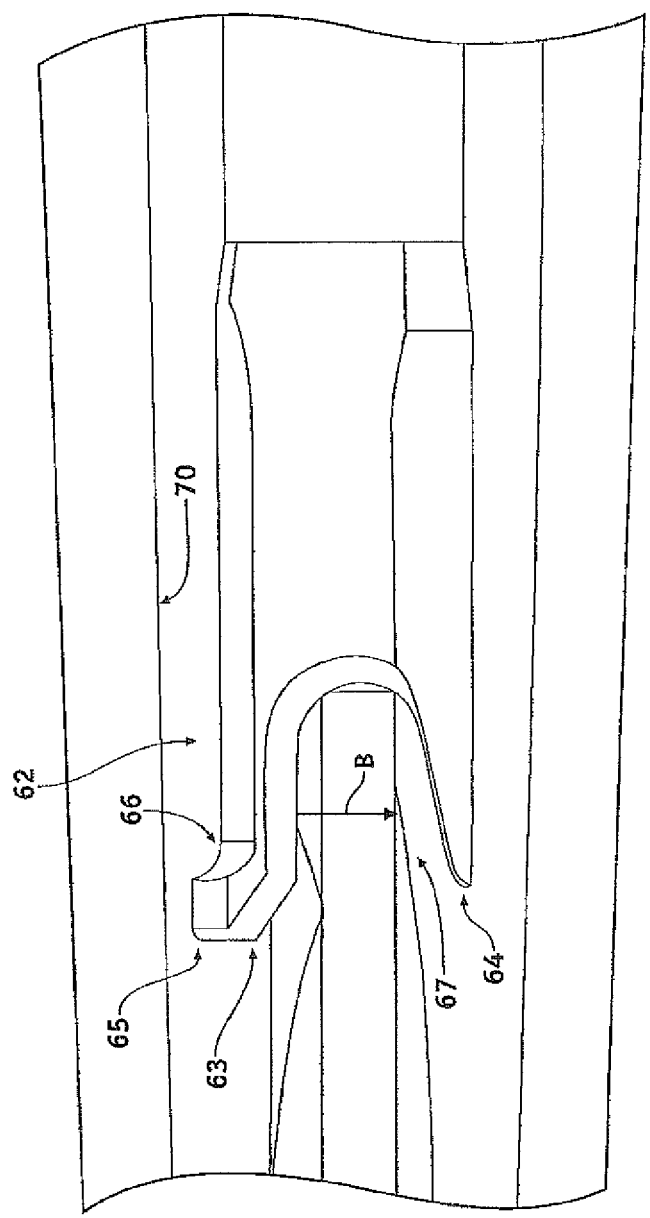
FIG. 19A is a side view of a pushrod according to an embodiment.
Figure 19D:
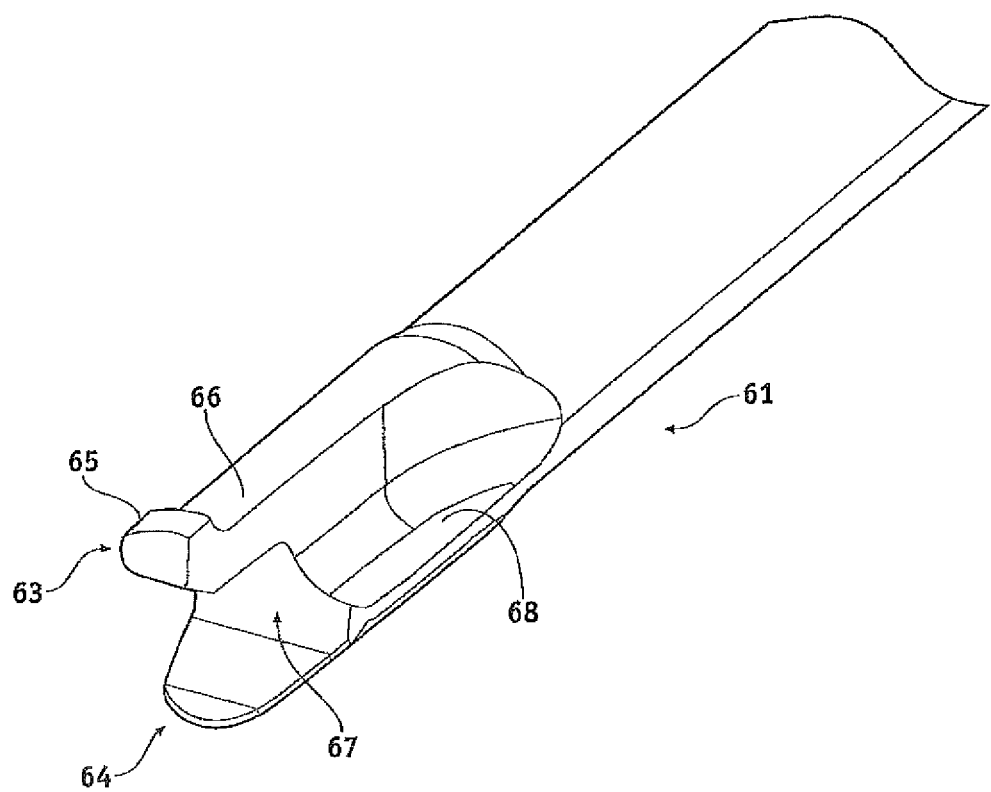
FIG. 19D is a perspective view of pushrod according to an embodiment of the invention.
Figure 19G:
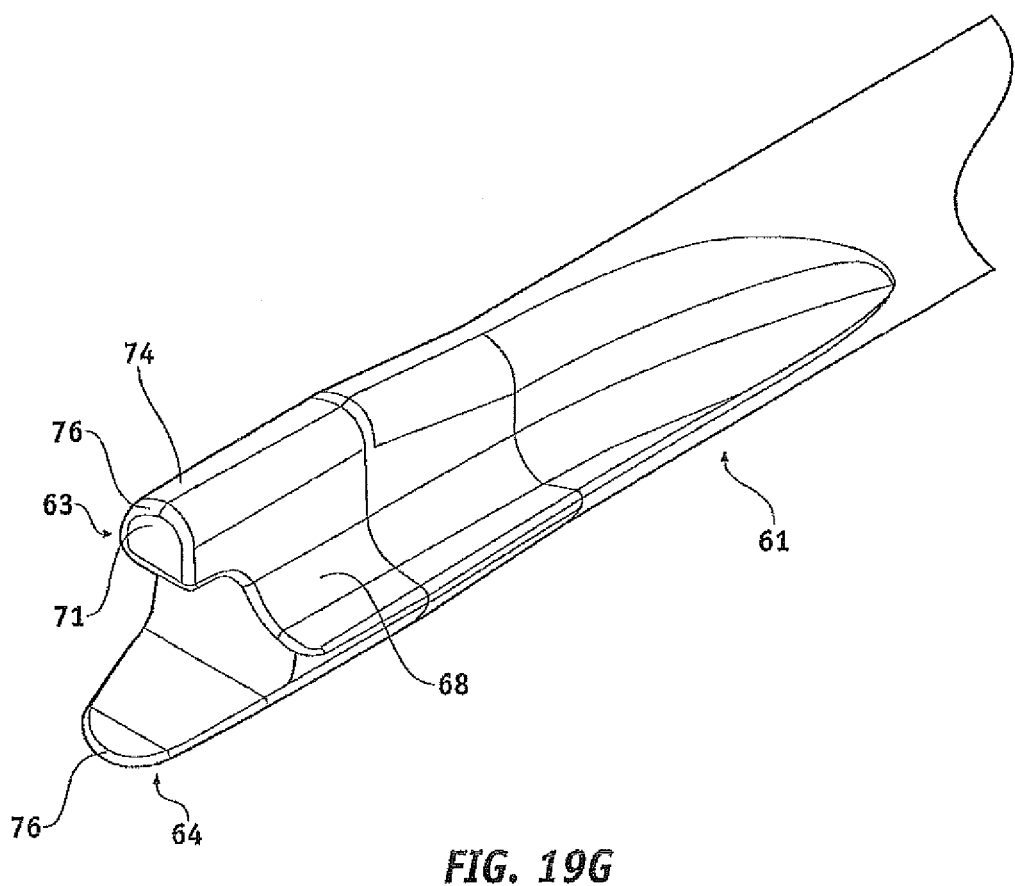
FIG. 19B is a side view of a pushrod according to an embodiment.
FIG. 19C is a side view of a pushrod according to an embodiment.
FIG. 19E is a side view of a pushrod according to an embodiment.
Figure 19H:
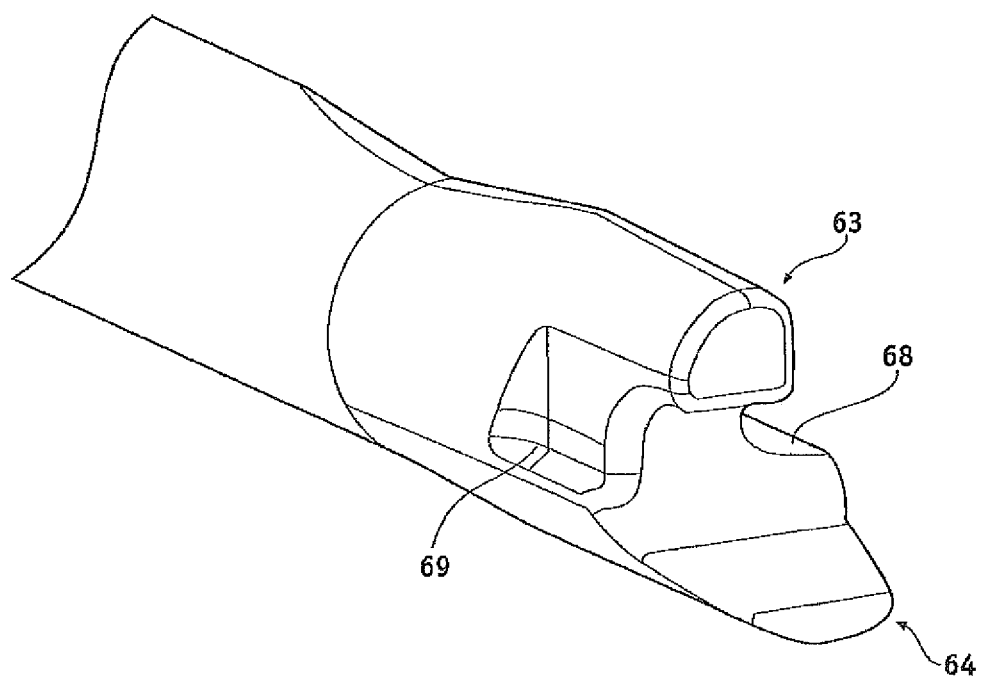

FIG. 19A illustrates a pushrod capable of being used with the system 20. Pushrod 61 comprises a top jaw 63 and a bottom jaw 64 that form mouth 67. Top jaw 63 may also comprise a lip 65 that protrudes from an upper portion 66 of top jaw 63. In an embodiment, lip 65 is configured and dimensioned to help catch trailing haptic 36 and keep trailing haptic 36 in a swept/folded configuration. FIG. 19D illustrates an exemplary pushrod of the present invention modifying the features of FIG. 19A. In FIG. 19D a portion of the distal end of pushrod 61 is removed resulting in cutout portion or notch 68 to allow room for the IOL as it is folded and/or compressed during insertion of the IOL into an eye. The cutout portion 68 of pushrod 61 provides for less force on the walls of delivery tube 26 and less force on the IOL as it delivered preventing damage to the IOL and delivery tube 26. In an embodiment, cutout portion 68 comprises approximately half the diameter of the top jaw 63 for a portion of the distal end including the lip 65, while bottom jaw 63 remains intact. Cutout portion 68 may extend proximally beyond top jaw 63 into the body of pushrod 61. In an embodiment, a notch or cutout portion may also extend or be placed into bottom jaw 64. It is also envisioned that an additional notch or cutout similar to notch 68 can be made on the opposite side of top jaw 63. Bottom jaw 64 may also have one or more notches. In an embodiment, a cross-section view of cutout portion 68 shows an L-shaped seat (see FIG. 20).

In an embodiment, lip 65 is configured to ride along at least a portion of an internal channel or groove located within handpiece 22. Lip 65 provides more stability for the pushrod 61 as it is advanced within a lumen of the handpiece 22 towards the distal end of the handpiece. By having the lip 65 engage at least a portion of the internal channel, the distal end of the pushrod is less likely to move from its desired location within the lumen as the pushrod is advanced towards the distal end of the handpiece.

According to an embodiment, the distal end of pushrod 61 may have a top jaw 63 and a bottom jaw 64 that form mouth 67 as illustrated in FIG. 19E-19H. As shown in FIG. 19E, top jaw 63 is shorter in length than bottom jaw 64 and includes cutout portion 68. For such an embodiment sweeping of the trailing haptic by pin 100 or another means is unnecessary because the design of the distal end of pushrod 61 causes the trailing haptic of an IOL to be swept or folded over the optic as the pushrod assembly 60 travels down the lumen of the insertion system towards the distal end of the delivery tube. In an embodiment, the top jaw is designed to engage the trailing haptic of an IOL before the bottom jaw engages the lens body or edge of the optic. In an embodiment, the height of the top jaw is such that it configured to couple with at least a portion of an internal channel of the handpiece, preferably the top jaw is configured to couple with at least a portion of an internal channel located in the staging area, more preferably the top jaw is configured to couple with an internal channel extending through the staging area. In another embodiment, the blunt tip may a height that is larger than the height of a haptic, e.g. a trailing haptic.

In an embodiment, the distal end of pushrod 61 may comprise another cutout portion 69 on the opposite side of the first cutout portion. The second cutout portion 69 may also provides for less force on the walls of delivery tube 26 and less force on the IOL as it delivered preventing damage to the IOL and delivery tube 26. For example, as the IOL is advanced down the delivery tube, the IOL is compressed. The second cutout portion 69 provides space for an edge of the IOL to wrap around the top jaw 63 and tuck into the second cutout portion 69. The second cutout portion may be shorter or longer in length than the first cutout portion 68, preferably shorter than the first cutout portion 68. The width of the second cutout portion may be larger or smaller than the width of the first cutout portion, preferably small that the width of the first cutout portion. The second cutout portion 69 may create a substantially L-shaped seat. In an embodiment, a notch or cutout portion may also extend or be placed into bottom jaw 64. It is also envisioned that an additional notch or cutout similar to cutout portion 68 and 69 can be made on one or both sides of bottom jaw 64.

Similar to the lip 65 discussed above, in an embodiment, the top jaw 63 illustrated in FIG. 19E-19H is configured to ride along at least a portion of an internal channel or groove located within handpiece 22. Coupling of the top jaw 63 with at least a portion of an internal channel provides more stability for the pushrod 61 as it is advanced within a lumen of the handpiece 22 towards the distal end of the handpiece. By having the at least a portion of top jaw 63 engage at least a portion of the internal channel, the distal end of the pushrod is less likely to move from its desired location within the lumen as the pushrod is advanced towards the distal end of the handpiece. The forces generated by moving the IOL down the lumen of the staging area and/or lumen of the cartridge can have a tendency to push or offset the distal end of the pushrod. Coupling the top jaw 63 with at least a portion of the internal channel or groove helps to counter this movement and maintain the distal end of the pushrod in proper alignment, e.g. maintaining the distal end of the pushrod substantially on center of the lumen of the handpiece. In an embodiment, the internal channel or groove runs the length of the staging area.

In an embodiment, the top jaw 63 may have a blunt tip 71 and a rounded top portion 74. The blunt tip 71 sweeps or folds the trailing haptic of an IOL over the optic as the pushrod assembly 60 travels down the lumen of the insertion system towards the distal end of the delivery tube. The top jaw 63 and the bottom jaw 64 may have a rounded leading edge 76. Rounding the leading edge prevents damage to an IOL as it is moved down the lumen of an insertion system.

In an embodiment, pushrod 61 has a tapered portion around the circumference of the pushrod starting at or near the back of mouth 67 and extends a long a length of the pushrod. In an embodiment, the tapered portion extends approximately ⅔ the total length of pushrod 61. As shown in FIG. 19F, beginning at or proximally near the back of the mouth 67, the diameter of the tapered portion gradually gets smaller until approximately the midline of the tapered portion and then begins to gradually get larger until it reaches the largest diameter of the pushrod 68. The smallest diameter of the tapered portion may occur at the halfway point of the entire length of the tapered portion. In an embodiment, the smallest diameter occurs beyond the halfway point of the entire length of the tapered portion in the proximal direction. The length of the tapered portion may be between about 0.280 in. (7.122 mm) and about 0.325 in. (8.255 mm). The diameter of the pushrod at its largest diameter may be between about 0.080 in. (2.032 mm) and about 0.060 in. (1.524 mm), preferably 0.070 in. (1.778 mm); and the smallest diameter of the tapered portion may be between about 0.045 in. (1.143 mm) and about 0.060 in. (1.524 mm). The tapered portion provides for space and/or allows for a trailing haptic to wrap around the pushrod should the haptic not fold over the optic, which prevents the IOL from being damaged or broken off from the rest of the IOL.

In an embodiment, cutout portion or notch 68 may extend into a portion of the tapered portion. Cutout portion 68 is designed as a safety feature to (1) provide space for the folding IOL as it is advanced down a tapered lumen; (1) allow for a trailing haptic to wrap around the pushrod and/or guide the trailing haptic around the tapered portion should the haptic not fold over the optic; (3) allow for extension of a trailing haptic that does not get folded; and/or (4) allow space for shoulder or bend that is created near the optic-haptic junction when the trailing haptic is folded over the optic, which prevents the IOL from being damaged or broken off from the rest of the IOL. In an embodiment, the cutout portion 68 may have a length between about 0.150 in. (3.81 mm) and about 0.300 in. (7.62 mm), a height between about 0.030 in. (0.762 mm) and about 0.050 in. (1.27 mm), and a width between about 0.040 in. (1.016 mm) and about 0.065 in. (1.651 mm). The length of the cutout portion 68 may also be longer or shorter than the full extension of an IOL haptic. Cutout portion 68 may begin at or near the tip of pushrod 61 or at or near the back of the mouth 67 and continue a length of the pushrod 61. The cutout portion 68 may continue a length of the pushrod 61 with its width gradually tapering out or becoming smaller until it meets the side of the pushrod (see FIG. 19G).

Figure 20:
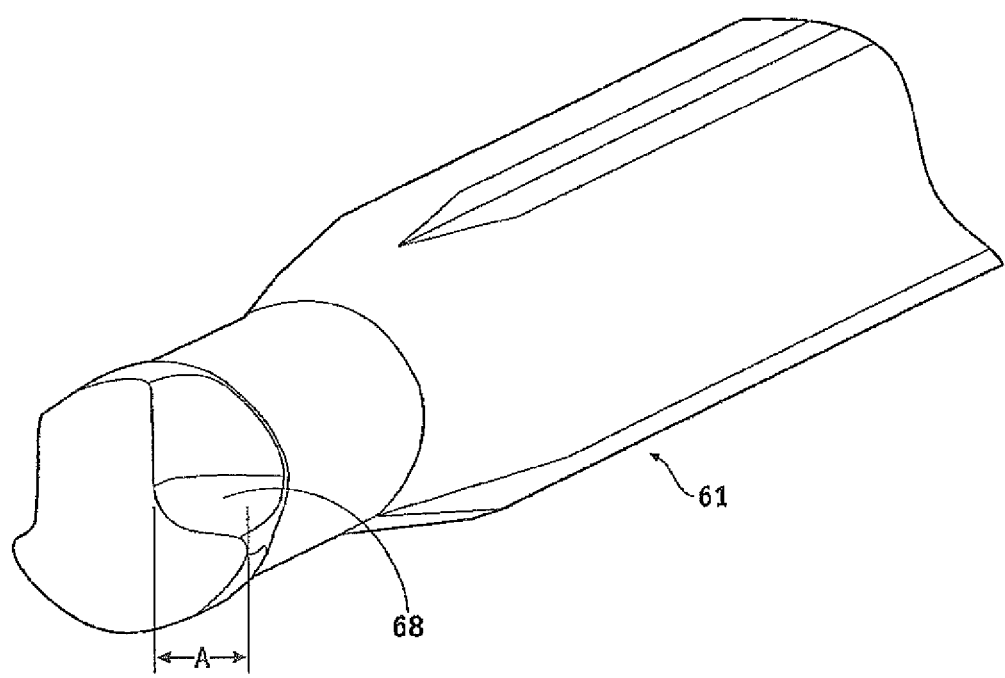
FIG. 20 is a cross-sectional perspective view of the pushrod in FIG. 19D.

The features of pushrod 61 as shown in FIGS. 19A-19D may have various dimensions. The length of the cutout portions 68 may be between about 0.145 in. (3.683 mm) to about 0.165 in. (4.191 mm), preferably between about 0.149 in. (3.7846 mm) to about 0.160 in. (4.064 mm), more preferably about 0.149 in. (3.7846 mm) or about 0.160 in. (4.068 mm). The width of upper portion 66 of top jaw 63 may range from about 0.015 in. (0.381 mm) to about 0.030 in. (0.762 mm), preferably about 0.023 in. (0.5842 mm). The diameter or width A of cutout portion 68 as shown in FIG. 20 may be between about 0.015 in. (0.381 mm) to about 0.025 in. (0.635 mm), preferably about 0.019 in. (0.4826 mm). According to an embodiment, the diameter A of cutout portion 68 may be inversely proportional to the width of the upper portion 66 of top jaw 63. The height of lip 65 that protrudes up may be between about 0.003 in. (0.0762 mm) to about 0.012 in. (0.3048 mm), preferably about 0.006 in. (0.1524 mm). In an embodiment, there may be a radius on the back side of lip 65 where lip 65 and upper portion 66 meet. The radius may be sharp to 0.010 R. In an embodiment, the radius of mouth 67 that engages a lens may range between 0.012 R-0.020 R, preferably about 0.014 R. The length of top jaw 63 and the bottom jaw 64 from the back of mouth 67 may be between about 0.045 in. (1.143 mm) and about 0.070 in. (1.778 mm). In an embodiment the length of top jaw 63 is preferably about 0.054 in. (1.3716 mm). The top jaw length may have a relationship (ratio) to the bottom jaw which is about 1.3 to 1 (Top to Bottom). In an embodiment, the relationship may be 1 to 1 or 1 to 1.3 (Top to Bottom).

The features of pushrod 61 as shown in FIGS. 19E-19H may have various dimensions. The length of the cutout portions 68 may be between about 0.150 in. (3.81 mm) to about 0.300 in. (7.62 mm), preferably between about 0.190 in. (4.826 mm) to about 0.250 in. (6.35 mm), more preferably about 0.190 in. (4.826 mm). The diameter or width of cutout portion 68 as shown may be between about 0.020 in. (0.508 mm) to about 0.030 in. (0.762 mm), preferably about 0.025 in. (0.635 mm). In an embodiment, the radius of mouth 67 that engages a lens may range between 0.010 R-0.018 R, preferably about 0.013 R. The width of the top jaw may be between about 0.020 in. (0.508 mm) and about 0.030 in. (0.762 mm) and the width of the bottom jaw may be between about 0.060 in. (1.524 mm) and about 0.040 in. (1.016 mm). The top jaw may be offset from a centerline along the longitudinal axis of the pushrod. The top jaw length may have a relationship (ratio) to the bottom jaw which is about 1 to 2 (Top to Bottom). In an embodiment, the relationship may be 1 to 1 or 1 to 1.3 (Top to Bottom). The width of the top jaw may have a relationship to the width of the bottom jaw which is about 1 to 2 (Top to Bottom). In an embodiment, where the top portion of the top jaw meets the side wall of the notch, the radius of curvature or blending may be about 0.010 R. Also, in another embodiment the length of the notch may be about 60% of the total length of the pushrod.

Pushrod Flex Tip

As discussed above, FIG. 5 shows an exploded view of pushrod assembly 60 which comprises pushrod 61, plunger 24, and nut lock 102.

According to an embodiment of the present invention, pushrod 61 comprises distal tip 62 at the distal end of pushrod 61 that has a top jaw 63 and a bottom jaw 64, which is shown in FIG. 19A. Top jaw 63 of distal tip 62 is capable of flexing toward bottom jaw 64 shown by arrow "B" to allow the distal tip 62 (or distal end) of pushrod 61 to pass through the tapered lumen of delivery tube 26. Top jaw 63 may comprise a lip 65 that protrudes from an upper portion 66 of top jaw 63 and is capable of making contact with the lumen of delivery tube 26. FIG. 19B illustrates lip 65 coming in contact with the lumen 70 of delivery tube 26 and top jaw 63 flexing toward bottom jaw 64. Lip 65 may make continuous or substantially continuous contact with the lumen of delivery tube 26 while pushrod 61 is moved longitudinal through delivery tube 26 to eject the IOL out the distal end of the delivery tube. FIG. 19C illustrates that once lip 65 of top jaw 63 exits delivery tube 26 at the distal end, top jaw 63 will flex substantially back into its original position. Lip 65 can be any configuration or shape that will allow for the flexing of top jaw 63 toward bottom jaw 64. Preferably top jaw 63 is slightly longer or longer than bottom jaw 64 to prevent the IOL from being captured between the two jaws and held after the IOL exits from the delivery tube. According to an embodiment, bottom jaw 64 may remain substantially stationary with respect to the rest of pushrod 61. In an embodiment, the flexible top jaw 63 allows for further folding of the trailing haptic of the IOL over the optic during implantation of the IOL. The distal tip keeps the trailing haptic in a stable position.

In an embodiment, lip 65 may be located on the bottom jaw 64 depending upon the geometry of the IOL and/or haptic. For example, if instead of the trailing haptic being in a "C" configuration if you look at the IOL in an insertion device from the top, the trailing haptic is in reversed "C" configuration, the lip 65 may function better or properly if it is located on the bottom jaw 64.

In an embodiment, the bottom jaw 64 may also flex or be capable of flexing toward top jaw 63 to allow the distal tip (or distal end) of pushrod 61 to pass through the tapered lumen of delivery tube 26. It is also envisioned that both the top jaw 63 and bottom jaw 64 flex towards each other as the pushrod 61 is passed through the tapered lumen of delivery tube 26.

Tip Protector

Figure 21:
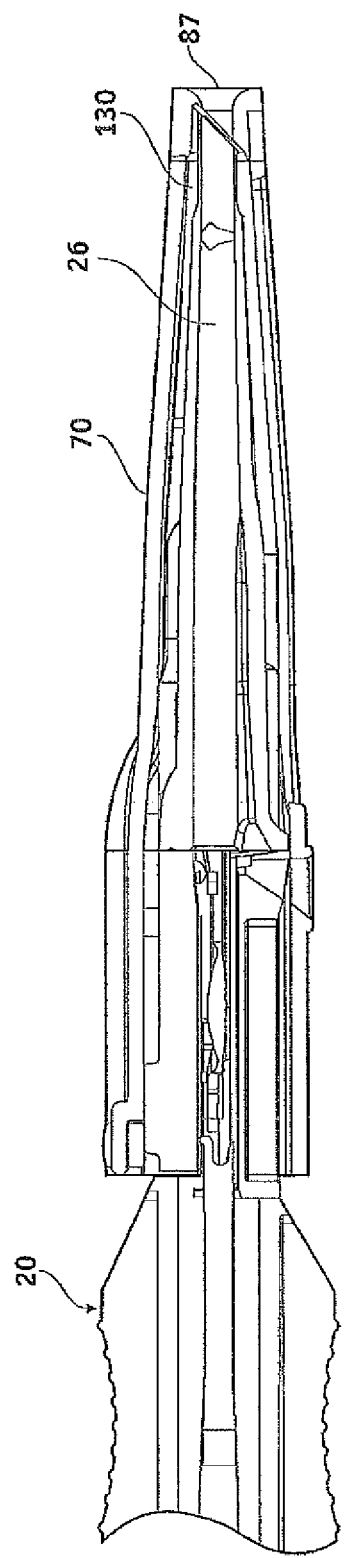
FIG. 21 is a cross-sectional view of a puller cap and insertion system according to an embodiment of the invention.

An advantage of puller cap 70 is it acts as a tip protector to prevent damage or deformation. As illustrated in FIG. 21, a certain amount of clearance or space is provided around the distal end of delivery tube 26 when puller cap 70 is placed onto system 20. The clearance or space 130 is maintained by contact between the internal structures of puller cap 70 at the proximal end and system 20. In an embodiment, clearance or space 130 between delivery tube 26 and the distal end of puller cap 70 is maintained by contact between wall 98 through window 97 shown in FIG. 15 and wings 27 and portion 96 of lock 95A, B shown in FIG. 7. It is also envisioned that other similar structures may be used to maintain clearance 130 to protect the tip of delivery tube 26.

Protective Cap

FIGS. 22A-G, 23A-B, 24, 25, and 26 illustrate a protective cap 200 of the present invention. Protective cap 200 has similar advantages of puller cap 70 of protecting the tip from damage or deformation. Protective cap 200 may be used instead of puller cap 70 when the trailing haptic is swept or folded by means of the pushrod or the trailing haptic does not require sweeping or folding. Protective cap 200 comprises finger grips 280, window 289, and port 287. Protective cap 200 may also comprise one or more of the following: clips (or snaps) 220, relief slots 225, and/or guides 235. Protective cap 200 may also comprise a fill indicator 255 and/or a material relief 265.

Protective cap 200 may be made of any material known in the art, preferably polypropylene, polycarbonate, polyethylene, or polyethylene terephthalate; more preferably polypropylene and polycarbonate; most preferably polypropylene. Protective cap 200 may also be of any color, preferably translucent or clear to enable a user to visualize the features inside protective cap 200 and anything housed within protective cap 200. Protective cap 200 may be the shape as illustrated in the embodiment in FIGS. 22A-G, but the invention also envisions that protective cap 200 may be of any shape or size to accommodate the needs of the insertion system the protective cap is used with or the needs of the user the puller cap is designed for. For example, the protective cap may be of an arrow shape as illustrated in the embodiment in FIG. 22B, may be more of a round shape, triangular shape, square shape, or shaped to meet the needs for shipping or handling.

The finger grips 280 may be of any design or configuration known in the art. According to an embodiment of the present invention, finger grips 280 may comprise a texture design or feature to ease gripping or actuation of the clip 220 and removal of protective cap 200 from an insertion system, such as system 20 as illustrated in FIGS. 1-5 and 1A-4A. The protrusion 282 of finger grips 280 may also be of any shape, including but not limited to square, rounded, triangle, and any other shape known in the art that may assist in grasping protective cap 200. Finger grips 280 may have inner walls that are sized and shaped to couple with at least a portion of the wings 27 that run along the longitudinal axis of cartridge 28. The inner walls are configured and dimensioned to avoid damaging the distal end of the tip of the delivery tube 26 when protective cap 200 is placed on the insertion device. In an embodiment, finger grips 280 may have a radius of curvature that is similar to or mirrors the curvature of a user's finger to assist with gripping and removal of the protective cap 200.

In an embodiment, protective cap 200 comprises tapered portion 245 (shown in FIGS. 22B, 22G, 25, and 26). Tapered portion 245 may be configured and dimensioned to mirror or substantially mirror the shape and size of the cartridge and/or insertion device. In an embodiment, tapered portion 245 comprises a bevel 247 which mirrors bevel 23 (shown in FIGS. 2, 2A, and 5). The internal and external walls of tapered portion 245 may also remain uniform or substantially uniform with respect to each other from the beginning of the tapered portion to at or near the distal end of cartridge such that the walls run parallel to each other. It is also envisioned that the internal walls of the tapered portion mirror the external features of the cartridge or distal end of the insertion device and the external walls of the tapered portions remain substantial linear, for example without a bevel.

As shown in FIG. 24, the distal end 285 of protective cap 200 may comprise internal bevel 270. Internal bevel 270 is configured and dimensioned to match or substantially match or mate with the bevel of the tip (at the distal end) of delivery tube 26 of cartridge 28. When protective cap 200 is placed on system 20, internal bevel 270 is coupled with the bevel of the tip of delivery tube 26 of cartridge 28 and port 287, and with its funnel feature it creates a larger opening. As discussed above, the small nature of ports can make it very difficult for doctors, nurses, and/or staff to locate openings for inserting fluids. Port 287 with internal bevel 270 enables a user to more easily direct a cannula tip 101 into a delivery tube 26 or port 87 as illustrated in FIG. 8.

Figure 22A:
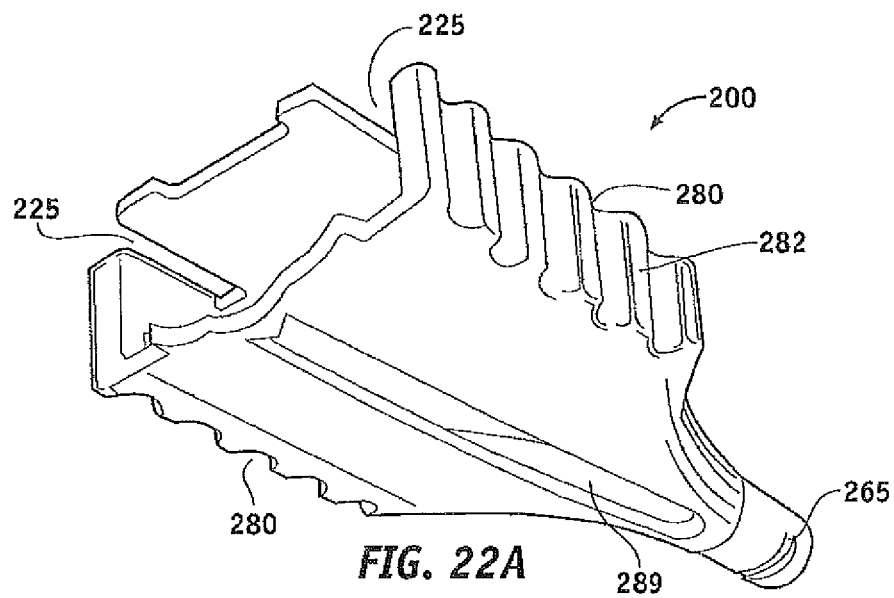
FIG. 22A is a perspective view of the protective cap according to an embodiment.

As illustrated in FIGS. 22A, C, E, and G, the distal end of protective cap 200 may also comprise a material relief 265. Material relief 265 helps prevent distortion of the tip at the distal end of protective cap 200 during the molding process. It is also envisioned, that the distal end of the protective cap 200 does not comprise a material relief.

As illustrated in FIG. 23A, protective cap 200 may also have inner walls comprising one or more internal guides 235 that run along at least a portion of the longitudinal axis and are configured and dimensioned to mate or couple with features on the outer portions of the insertion device. Internal guides 235 help keep the protective cap substantially aligned in a horizontal and vertical direction when the cap is placed on or removed. This helps to protect the distal end or tip of cartridge 28 or insertion system 20. The internal guides 235 may be of any width or of any length suitable to couple with external features of the insertion system and/or cartridge. According to an embodiment, there may be two internal guides on the internal wall of the protective cap along the longitudinal axis, and the distance between each of the guides may be any distance as long as it matches the external features on the insertion system. In an embodiment, the distance between the guides may be about 0.374 in. (9.4996 mm) apart. The width of a guide may be between about 0.023 in. (0.5842 mm) and about 0.028 in. (0.7112 mm), preferably about 0.025 in (0.635 mm). In an embodiment, the length of a guide may be between about 0.318 in. (8.0772 mm) to about 0.386 in. (9.8044 mm). The length of a guide may also be between about 0.318 in. (8.0772 mm) and about 0.328 in. (8.3312 mm), preferably about 0.323 in. (8.2042 mm) The length of the guide may also be between about 0.376 in. (0.5504 mm) and 0.386 in. (9.8044 mm), preferably about 0.381 in. (9.6774 mm) In another embodiment, one or more guides may begin at or near the distal end of relief slot 225 (see FIG. 23A) and extend for a distance toward the distal end of the protective cap.

As discussed above, the small nature of ports can make it very difficult for doctors, nurses, and/or staff to locate openings for inserting fluids. The protective cap 200 of the present invention solves this problem by providing a larger port 287 with a funnel feature that leads into the smaller port of the insertion device. This enables a user to more easily direct a cannula tip 101 into a delivery tube 26 or port 87 as illustrated in FIG. 8. The protective cap may also include one or more additional ports.

Protective cap 200 may also have one or more windows 289 to provide the users with a visual indicator of the amount of fluid inserted into the insertion system, as well as provide viewing of the distal end of a cannula tip. The one or more windows may be located on the top, bottom or sides of the protective cap, preferably on the top or the bottom. The one or more windows may also comprise a measuring devise such as a ruler to allow a user to measure the amount of fluid inserted into the inserter. The one or more windows may also comprise a material such that when a fluid is inserted into the inserter and viewed through the window light that is emitted through the window to the fluid is polarized providing a visual indicator of the fluid within the inserter. The window 289 may also comprise a fill indicator 255 to provide a maximum fill line.

Figure 22B:
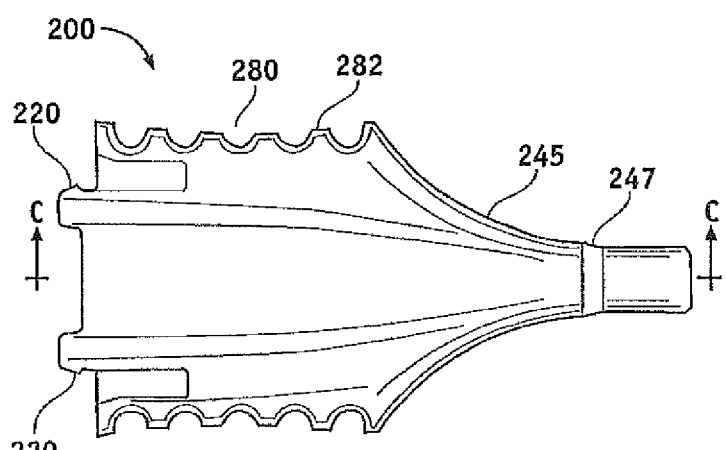
FIG. 22B is a top view of the protective cap according to an embodiment.
Figure 22C:
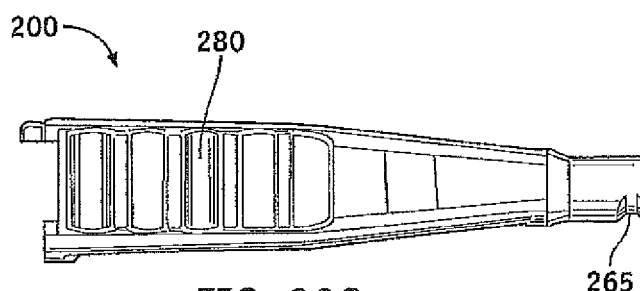
FIG. 22C is a side view of the protective cap according to an embodiment.
Figure 22D:
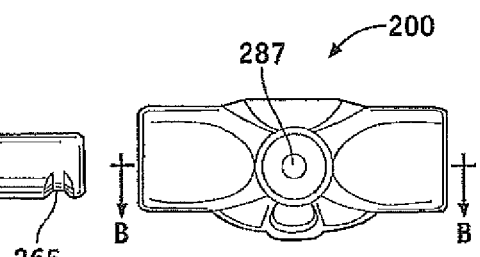
FIG. 22D is a front view of the protective cap according to an embodiment.
Figure 22E:
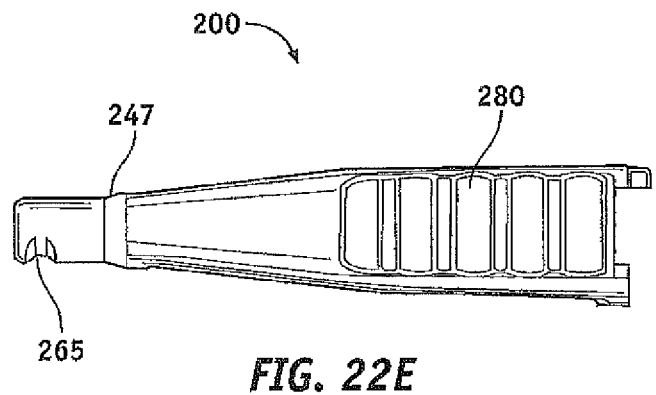
FIG. 22E is a side view of the protective cap according to an embodiment.
Figure 22F:
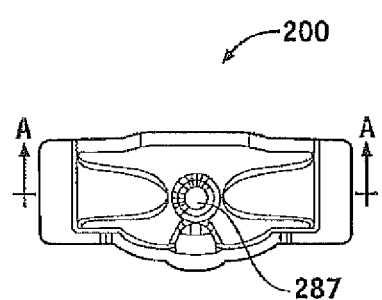
FIG. 22F is a rear view of the protective cap according to an embodiment.
Figure 22G:
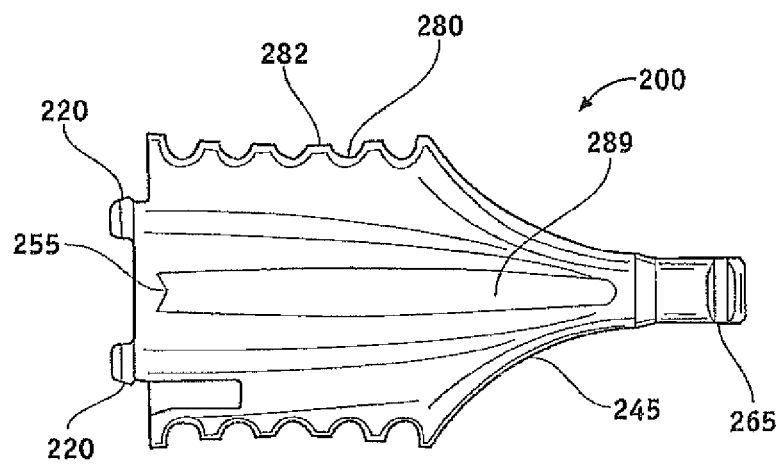
FIG. 22G is bottom view of the protective cap according to an embodiment.
Figure 25:
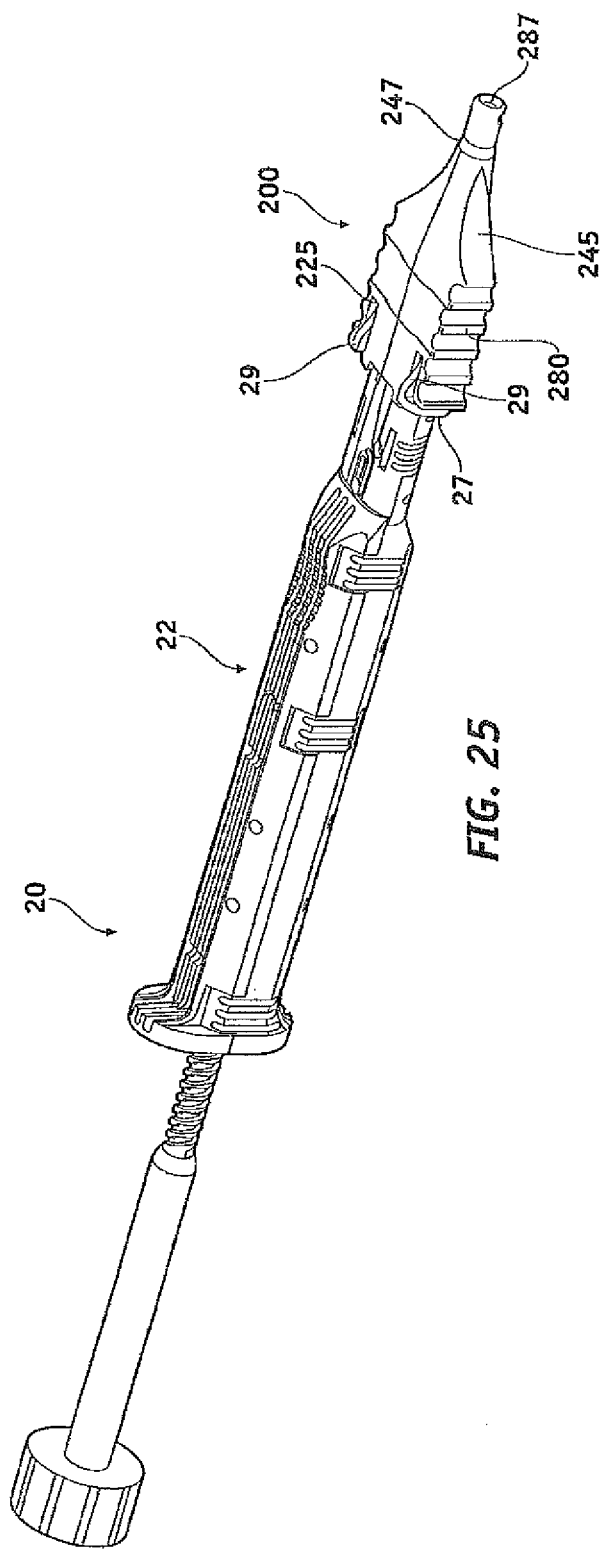
FIG. 25 is an assembled perspective view of an insertion system with a protective cap according to an embodiment of the invention.
Figure 26:
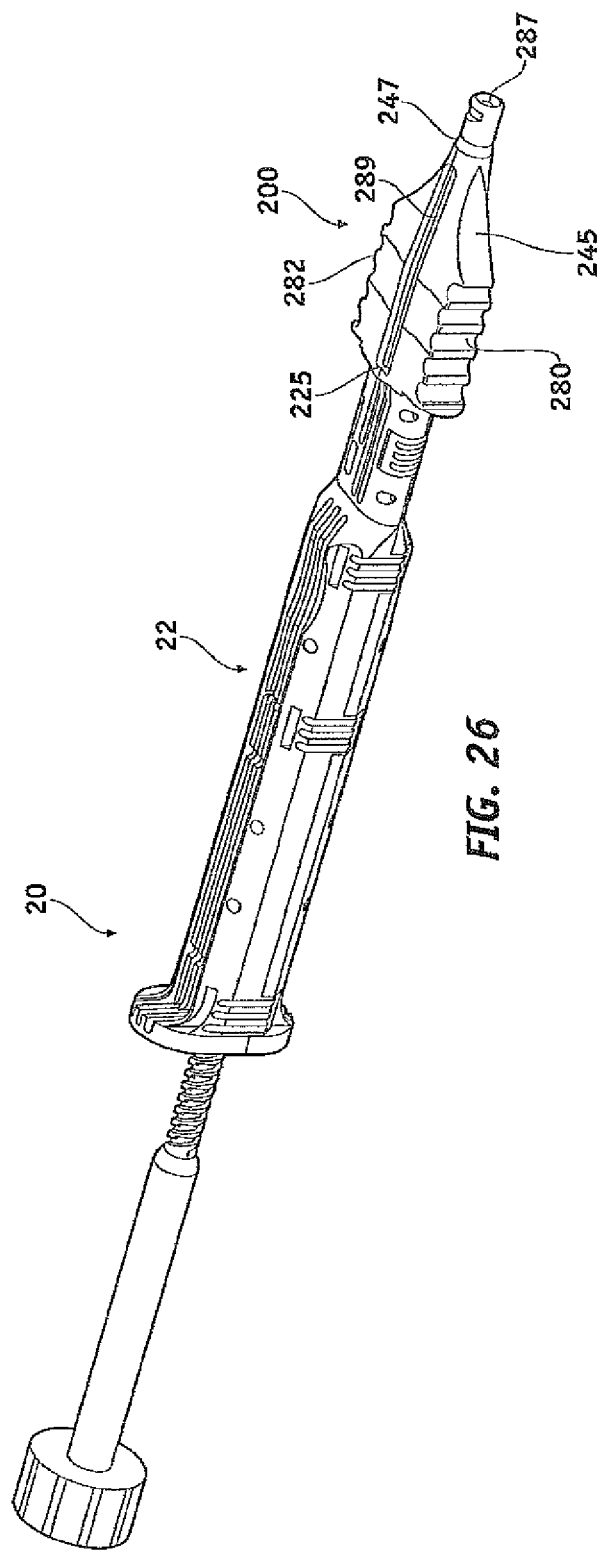
FIG. 26 is an assembled perspective view of an insertion system with a protective cap according to an embodiment of the invention
Figure 27A:
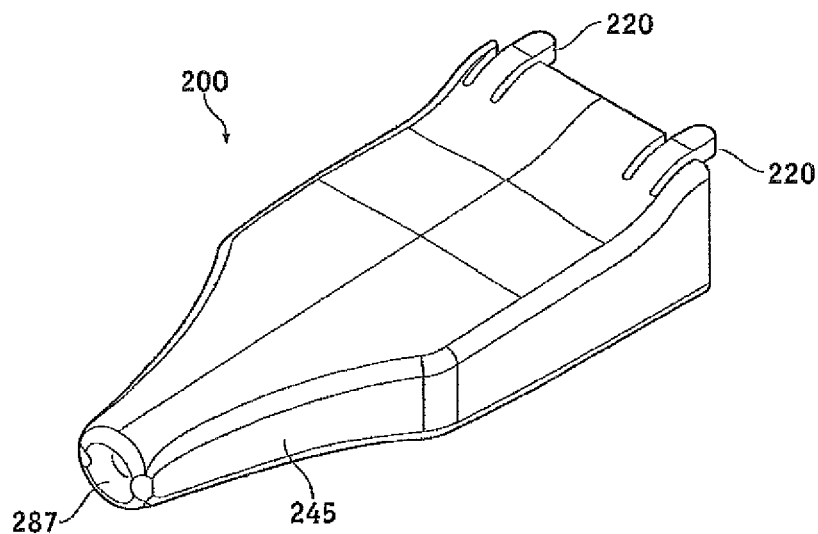
FIGS. 27A-F are additional embodiments of a protective cap.
Figure 27B:
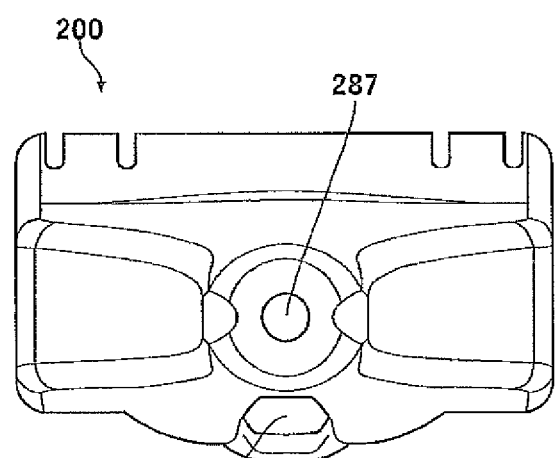
Figure 27C:
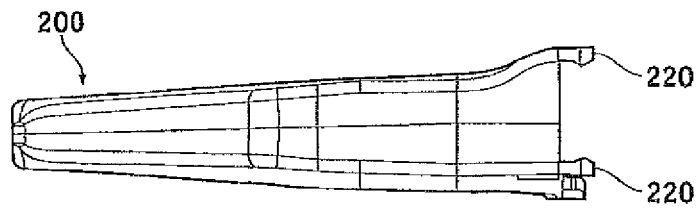
Figure 27D:
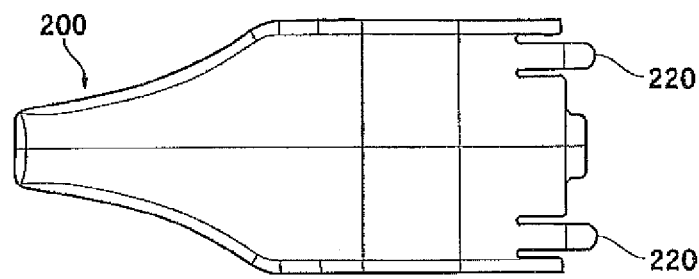
Figure 27E:
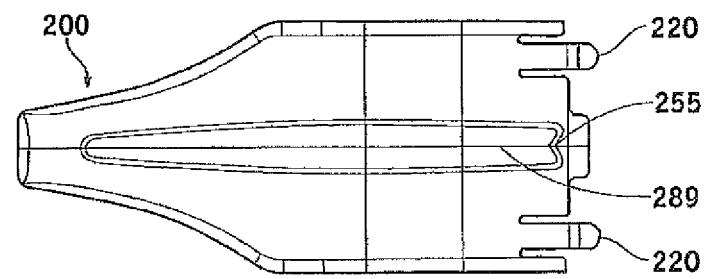
Figure 27F:
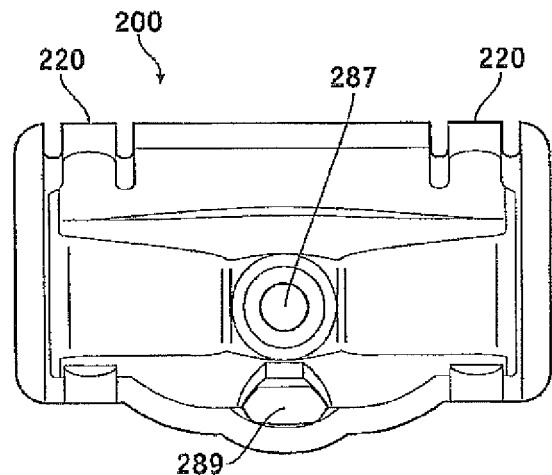
Figure 28A:
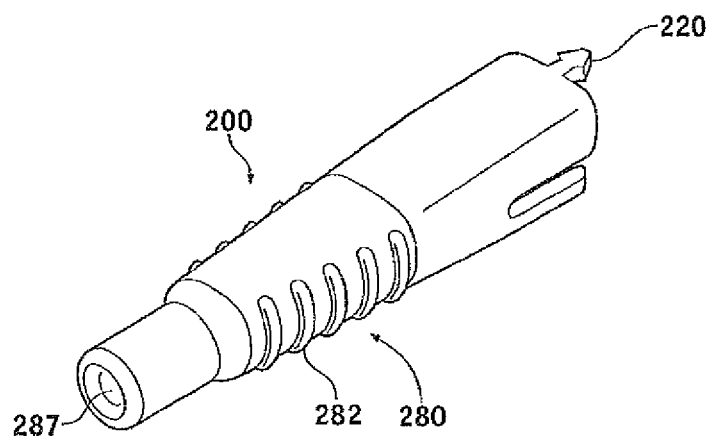
FIGS. 28A-F are additional embodiments of a protective cap.
Figure 28B:
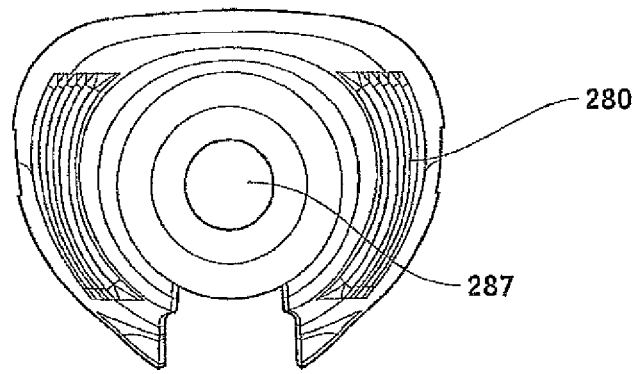
Figure 28C:
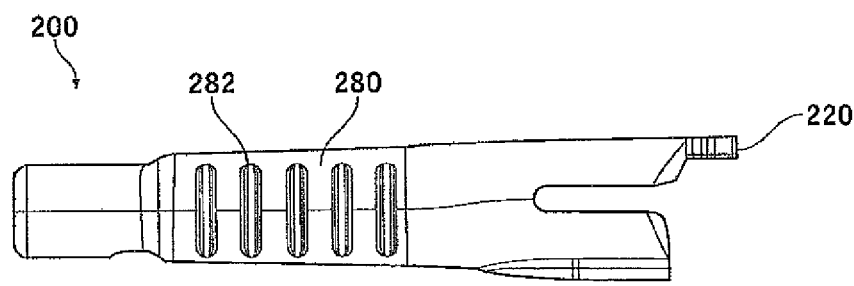
Figure 28D:
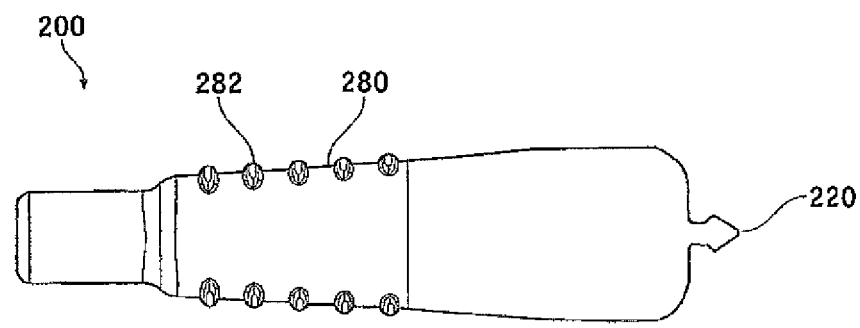
Figure 28E:
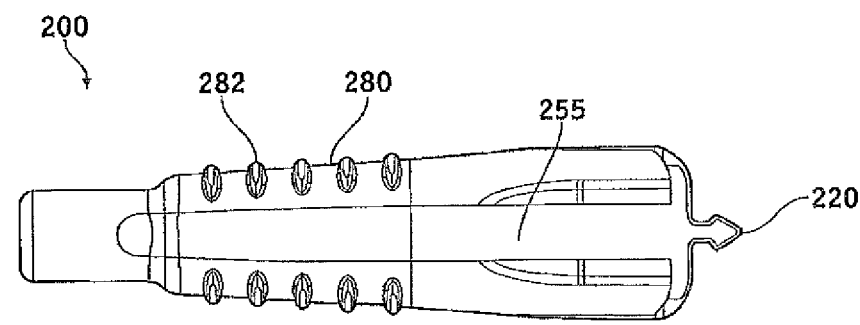
Figure 28F:
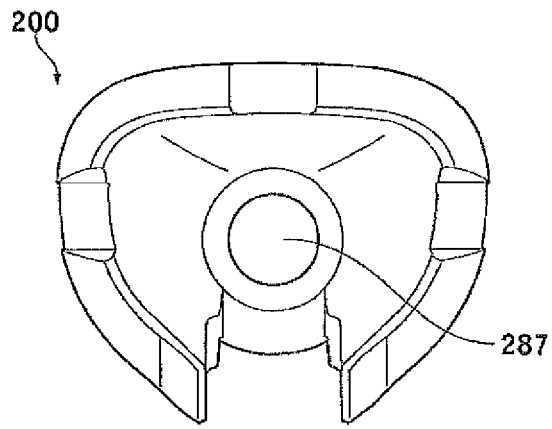
Figure 29A:
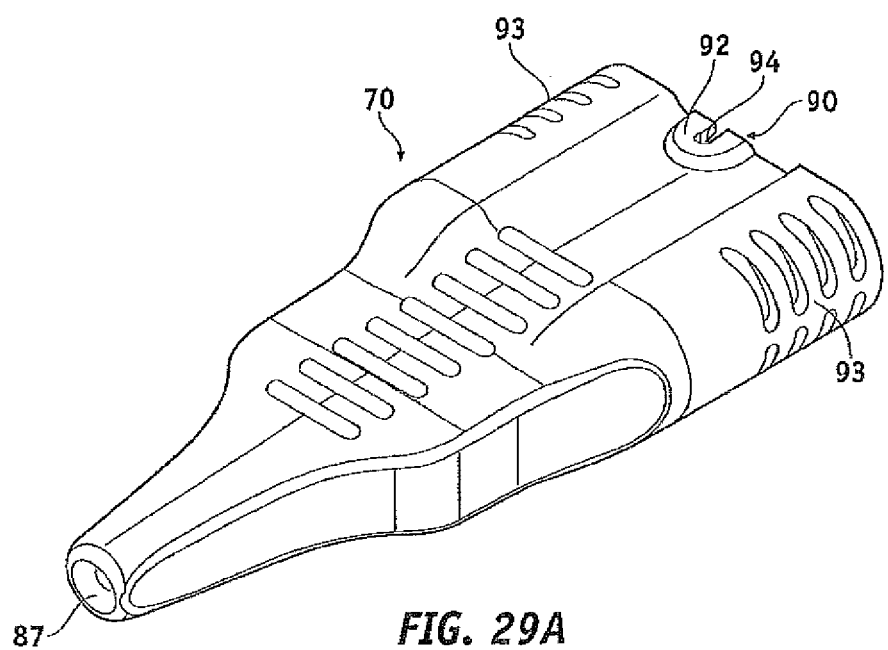
FIGS. 29A-F are additional embodiments of a puller cap.
Figure 29B:
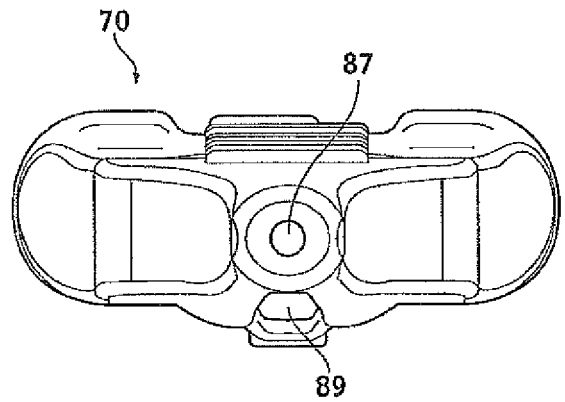
Figure 29C:
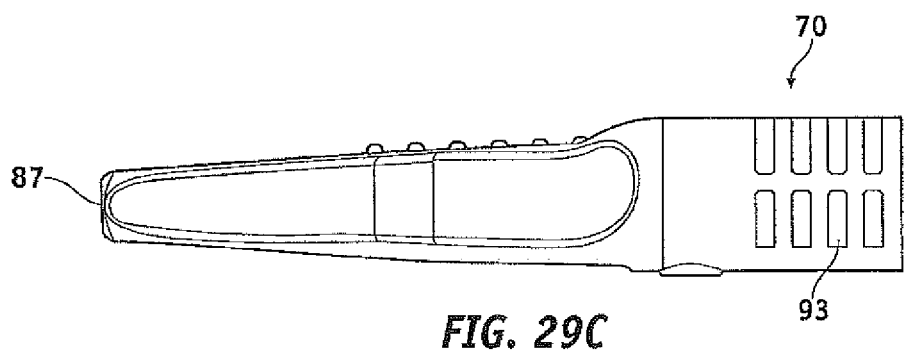
Figure 29D:
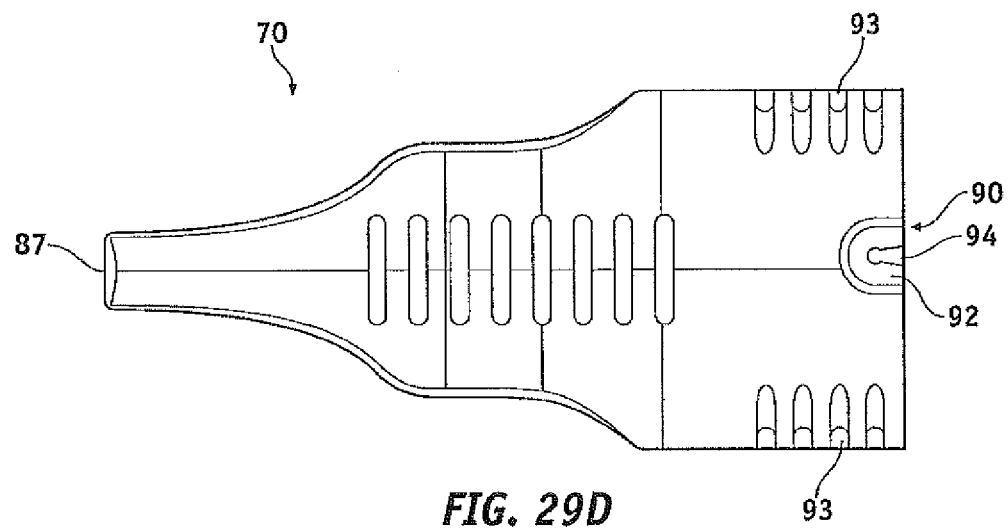
Figure 29E:
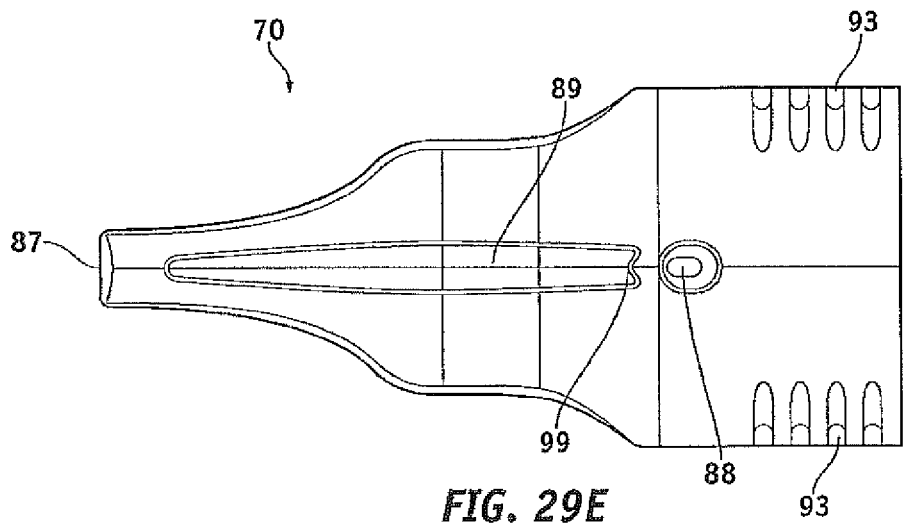
Figure 29F:
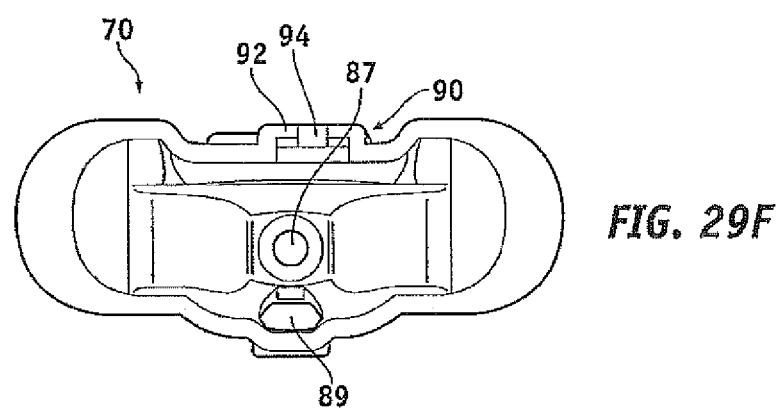
Figure 30A:
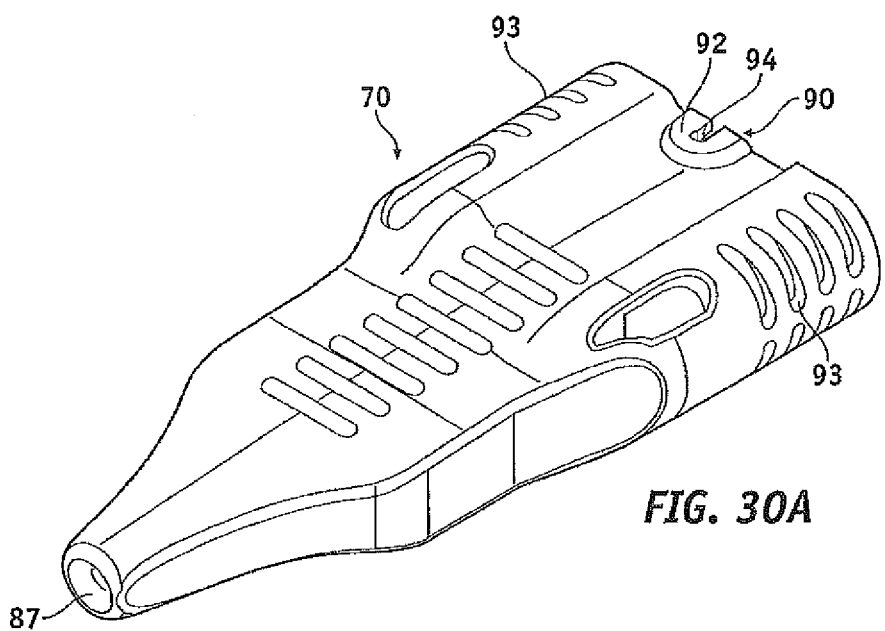
FIGS. 30A-F are additional embodiments of a puller cap.
Figure 30B:
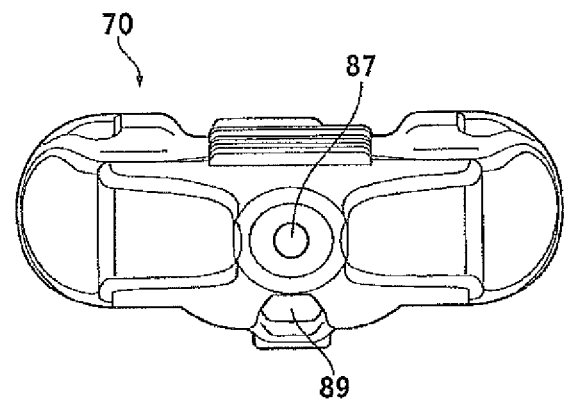
Figure 30C:
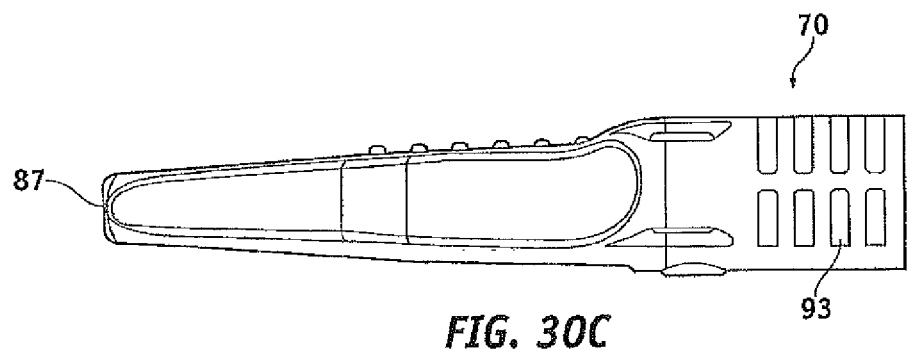
Figure 30D:
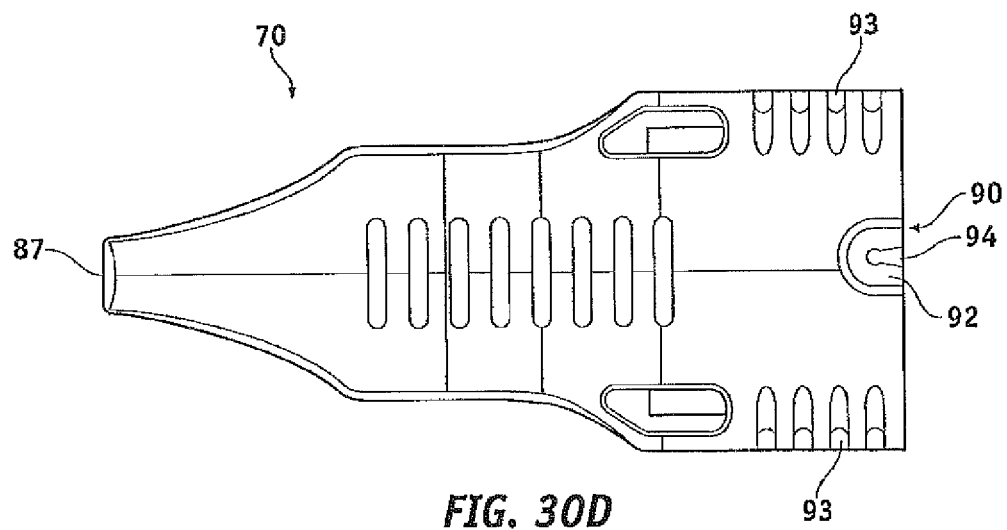
Figure 30E:
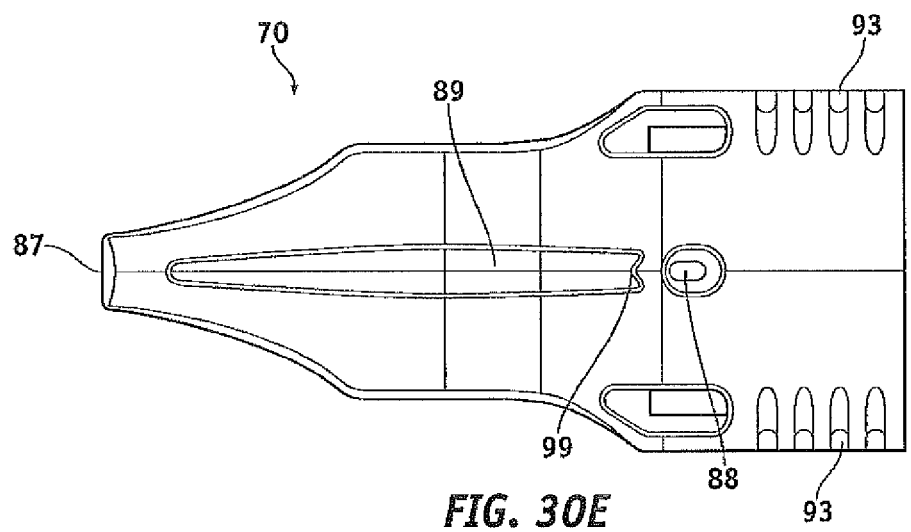
Figure 30F:
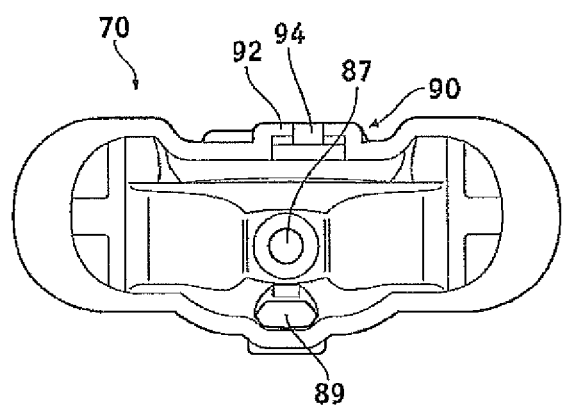

In order to secure protective cap 200 to an insertion system, such as the system 20 shown in FIGS. 1 and 1A, clip 220 may be used. Clip 220 is configured and dimensioned to mate with a distal portion of wings 27 of cartridge 28 (cartridge 28 is shown in FIG. 5). In an embodiment illustrated in FIG. 25, relief slots 225 of protective cap 200 couple with the vertical elements 29 (shown in FIG. 5) of wings 27 of cartridge 28. Relief slots 225 may be of any shape or size to couple with the shape or size of the vertical elements 29. Clip 220 may also extend beyond the proximal end of finger grips 280 as illustrated in FIG. 22B.

In an embodiment, when the protective cap 200 is placed on the distal end of the system 20, clips 220 act as a cantilever snap by riding along the vertical elements 29 of the wings 27 of cartridge 28 until the clips 220 are over center and then snapping down over the end of the wings 27. In an embodiment, the clip 220 is not located on the grip 280 to allow for easier removal of the protective cap. It is also envisioned that clip 220 may be located or coupled with the grip 280 depending upon the design and/or function of the clip 220 and whether the grip 280 is an extension of the clip 220.

FIGS. 27A-F and 28A-F illustrate additional embodiments of a protective cap with similar features as shown in FIGS. 22A-22G, 23A-23B, and 24. FIGS. 29A-F and FIGS. 30A-F illustrate additional embodiments of a puller cap with similar features as shown in FIGS. 6-13.

Plunger Marker

Figure 31A:
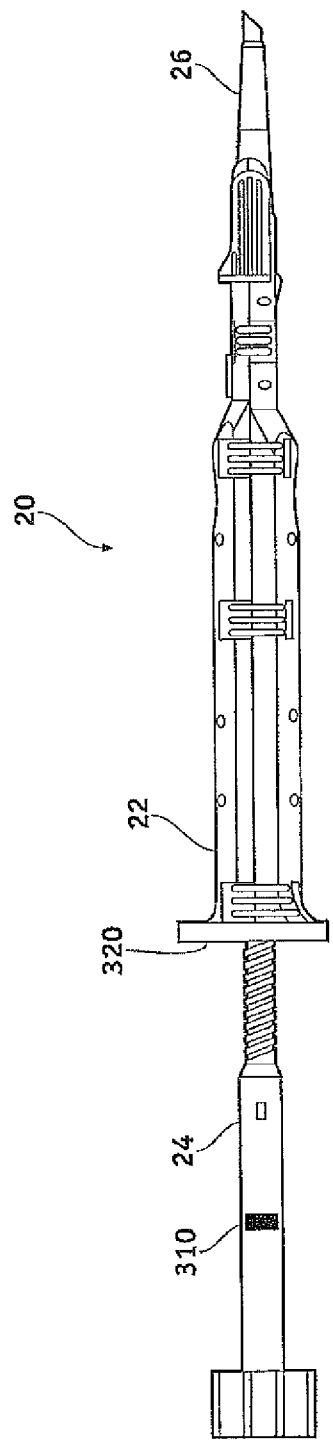
FIG. 31A is a side view of an insertion system according to an embodiment.
Figure 31B:
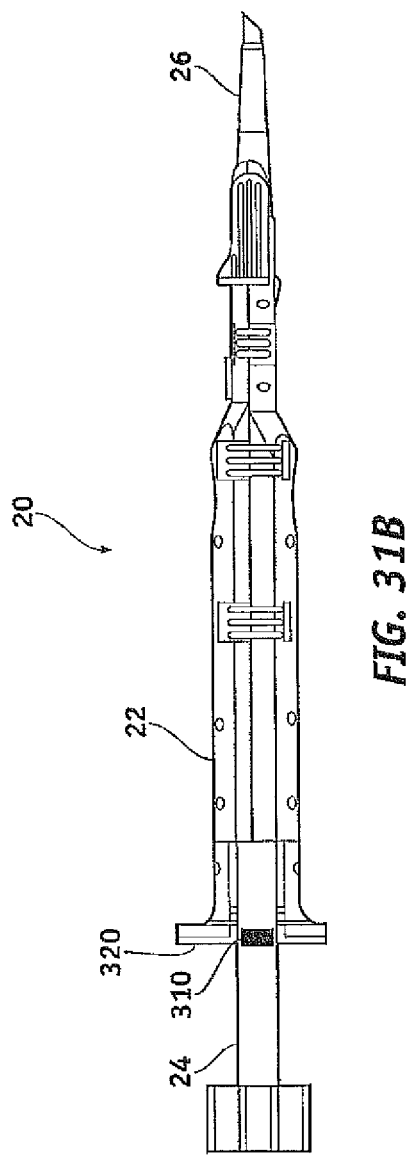
FIG. 31B is a side view with a cutout portion of an insertion system according to an embodiment.
Figure 31C:
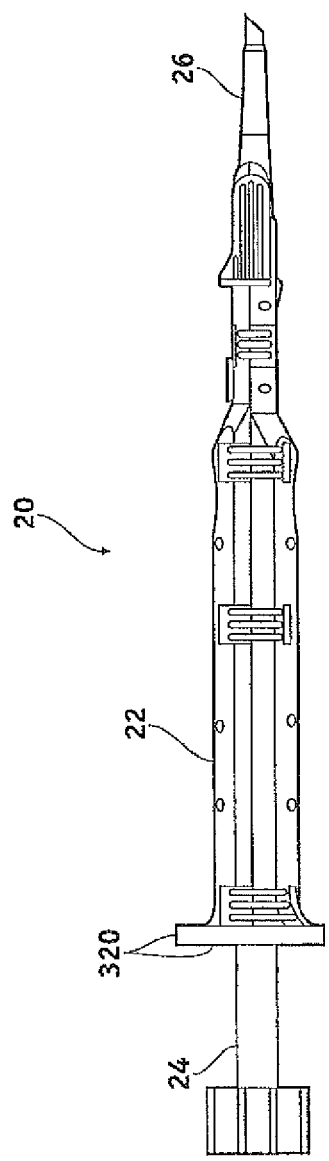
FIG. 31C is a side view of an insertion system according to an embodiment.

As illustrated in FIGS. 31A and 31B, plunger 24 may comprise a marker or indicator 310. As discussed above, the plunger 24 and/or pushrod 61 (pushrod assembly 60) translates axially through an elongate passage defined within the inserter handpiece 22 and is configured to urge the IOL from a holding station 30 through the distal delivery tube 26. In an embodiment, system 20 may operate in a push and/or twist fashion. With a push and twist mechanism, the plunger 24 may first be advanced axially along the longitudinal axis to a predetermined point and then the plunger 24 may be rotated for further advancement. Such a further advancement via rotation may provide additional control in the delivery of the IOL. In such a scenario, it would be helpful to provide an indication of when the axial translation of the plunger 24 or pushrod assembly 60 has reached the predetermined point. In such an embodiment, a marker 310 is placed on plunger 24 such that when the plunger 24 is advanced or displaced along the longitudinal axis of the system 20 a user will be able to visualize that the plunger has reached the predetermined point when marker 310 lines up with the proximal end 320 of handpiece 22 (see FIG. 31B) or disappears within handpiece 22 (see FIG. 31C). Marker 310 may be placed on any location on plunger 24 and may be of any shape, size or color. The predetermined point may be the proximal end 320 as described in the above embodiment, but it is also envisioned to be any location along the handpiece 22. This may be possible if handpiece 22 is made of a translucent or transparent material such that marker 310 is visible through handpiece 22.

Pushrod Supports

Figure 32:
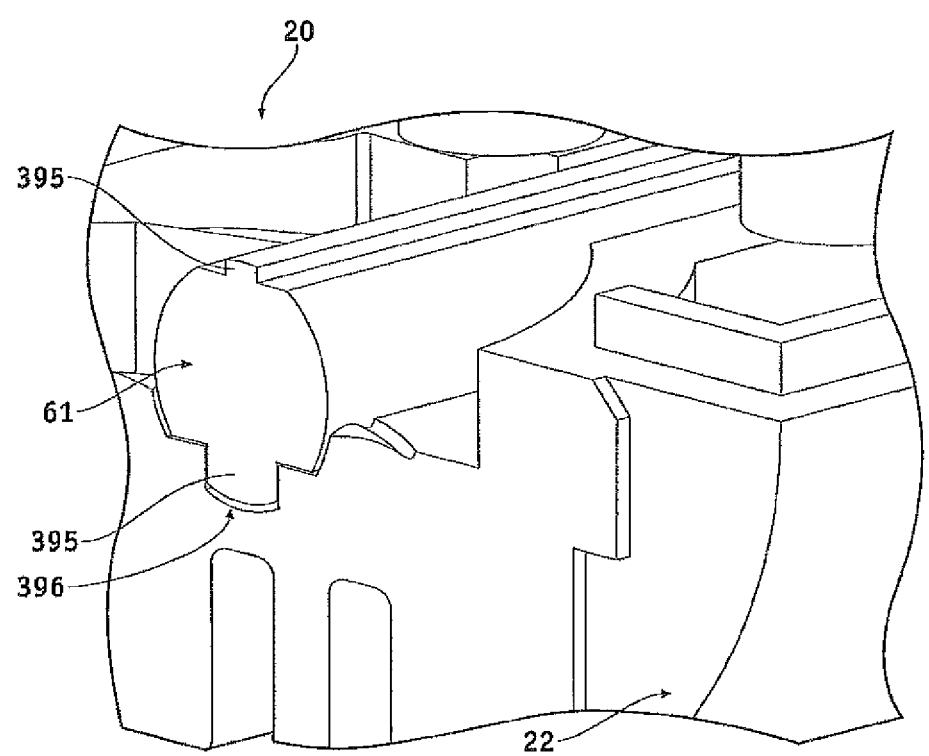
FIG. 32 is a cross-sectional view of a rails and channels embodiment.

According to an embodiment, the present invention provides one or more guide rails to provide support for the pushrod on the distal end of the inserter body. FIG. 32 shows a cross-sectional view of insertion system 20 with pushrod 61 and handpiece 22. According to an embodiment, pushrod 61 may comprise one or more guide rails 395, preferably a guide rail on opposite sides of pushrod 61. To mate with guide rails 395, one or more channels 396 on the upper and/or lower portions of lens holding station 30 may be included. The top and/or bottom channels 396 may be of any shape to mate with the shape of the one or more guide rails. Preferably the guide rails and channels are substantially rectangular in shape. Preferably, the lower channel is wider than the upper channel, although the width of the channels can be of any size and the channels can be of any shape. The guide rails on the pushrod mate to the channels and may have substantially the same shape. The guide rails may be on any portion of the pushrod and may make up any percentage of the pushrod. The channels may be located on other locations of the handpiece 22, including but not limited to base 52 and/or delivery tube 26.

According to an embodiment, it is also envisioned that one or more guide rails may be located on the handpiece 22 and corresponding channels may be located on the pushrod 61. In an embodiment, the channels may be located a long a portion of the pushrod 61 and may be found on any location around the circumference of the pushrod. The one or more guide rails may be located anywhere within the handpiece such that the guide rails are configured and dimensioned to mate with the one or more channels located on the pushrod 61.

Nut Lock

In insertion systems, advancing an IOL through a delivery tube involves a significant amount of force. To allow for advancement of an IOL from a lens storage area/holding station to a loading area the same mechanism described above can be used. For ease of use a pushing mechanism may be used to advance a lens from a storage/holding station into a delivery tube for insertion and then the same mechanism can be used to insert the IOL using a twisting mechanism. To allow for the push and twist and accommodate the high amount of force, the present invention incorporates a nut lock to prevent the pushrod from moving proximally as the pushrod is rotated to move the IOL distally.

Figure 33:
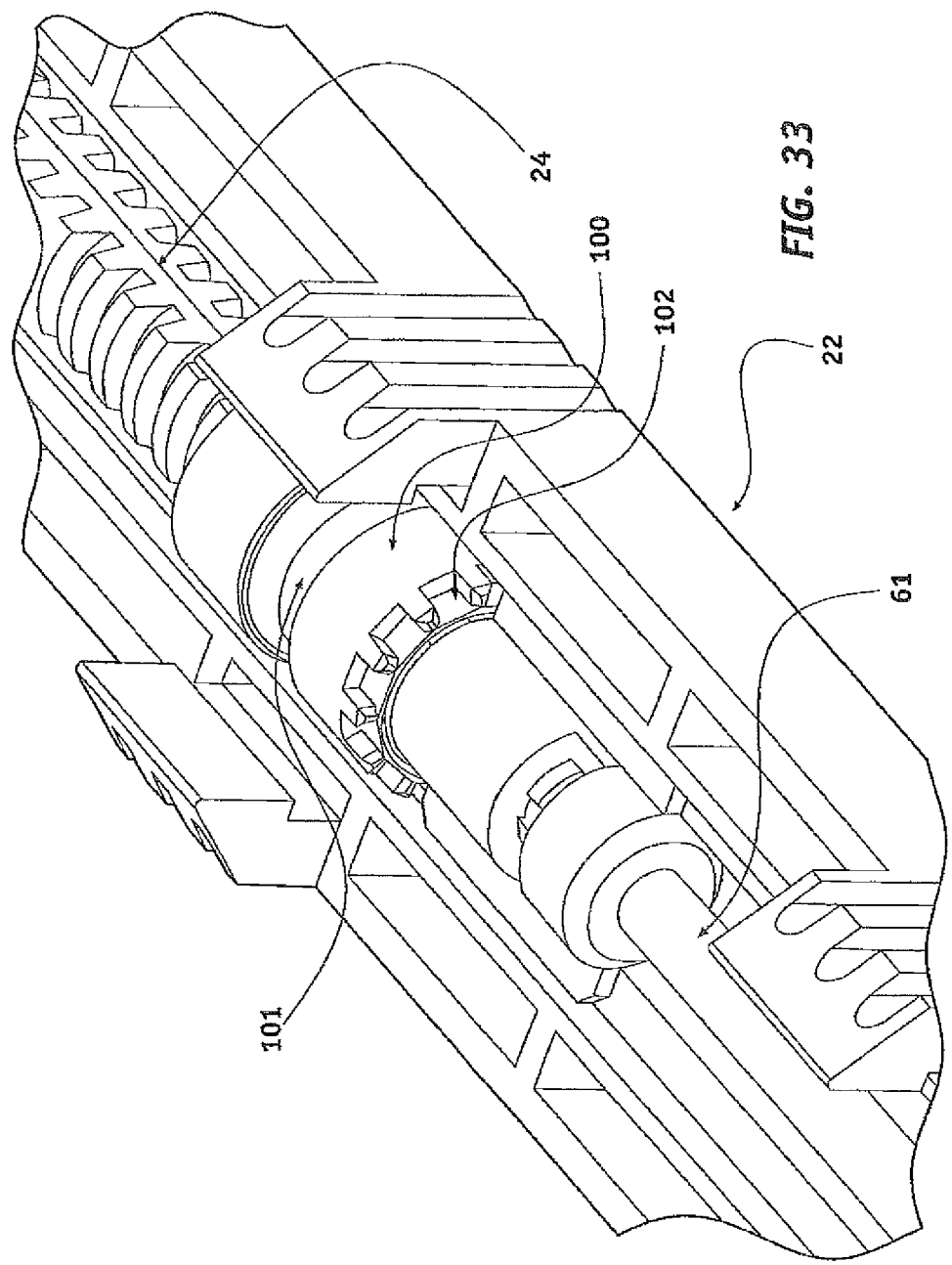
FIG. 33 is a perspective view of a nut lock according to an embodiment.

FIG. 33 illustrates an embodiment of the present invention. Nut lock 102 may have an internal thread of a load bearing quality. Nut lock 102 may be cylindrical in shape and have a centrally located groove 401 that allows interlock and/or detent with external/internal features of handpiece 22. On the distal portion of nut lock 102 there may be a series of radial keyways 402 that are capable of mating with keys (not shown) protruding inward from handpiece 22 that prevent it from counter rotating. Nut lock 102 may be made of any material known in the art, including but not limited to plastic, metal, and ceramic. Nut lock 102 may be coupled with the plunger 24 via load bearing threads and is sandwiched between plunger 24 and pushrod 61, which may be snapped together or coupled together in any way known in the art.

According to an embodiment, nut lock 102 may comprise a single lead thread, but may comprise more (multiple). Nut lock 102 may also have varying thread pitch.

According to an embodiment, when the insertion system is delivered to a physician's office, pushrod assembly 60 is in a first position. In this first position, the pushrod assembly 60 is in its most proximal position and groove 401 of nut lock 102 mates with one or more proximal detents 407 located at or near the most proximal end of handpiece 22 and prevents accidental movement of pushrod assembly 60. At this point, plunger 24 can be rotated in any direction without causing longitudinal movement of pushrod 61. When the pushrod assembly is moved into a second position between the most proximal detent 407 and a second distal detent 406, pushrod assembly 60 is movable in a longitudinal direction between detents, but rotation of plunger 24 in any direction does not longitudinally move pushrod 61. When pushrod assembly 60 is moved distally in a longitudinal direction to a third position, wherein groove 401 of nut lock 102 mates with one or more distal detents 406 (second detent position) (see FIG. 33A), pushrod assembly 60 is prevented from further distal or proximal movement by pushing or pulling on end cap 40. Once in the second detent position, the pushrod assembly cannot be pulled from this position back to the first proximal position. At this point the only way to advance pushrod 61 longitudinally to insert the IOL is to rotate plunger 24 via end cap 40 in either a clockwise or counter-clockwise direction (depending upon the configuration of the threads). This is to prevent reuse of a one time use insertion system and/or improper activation of the pushrod.

Figure 33A:
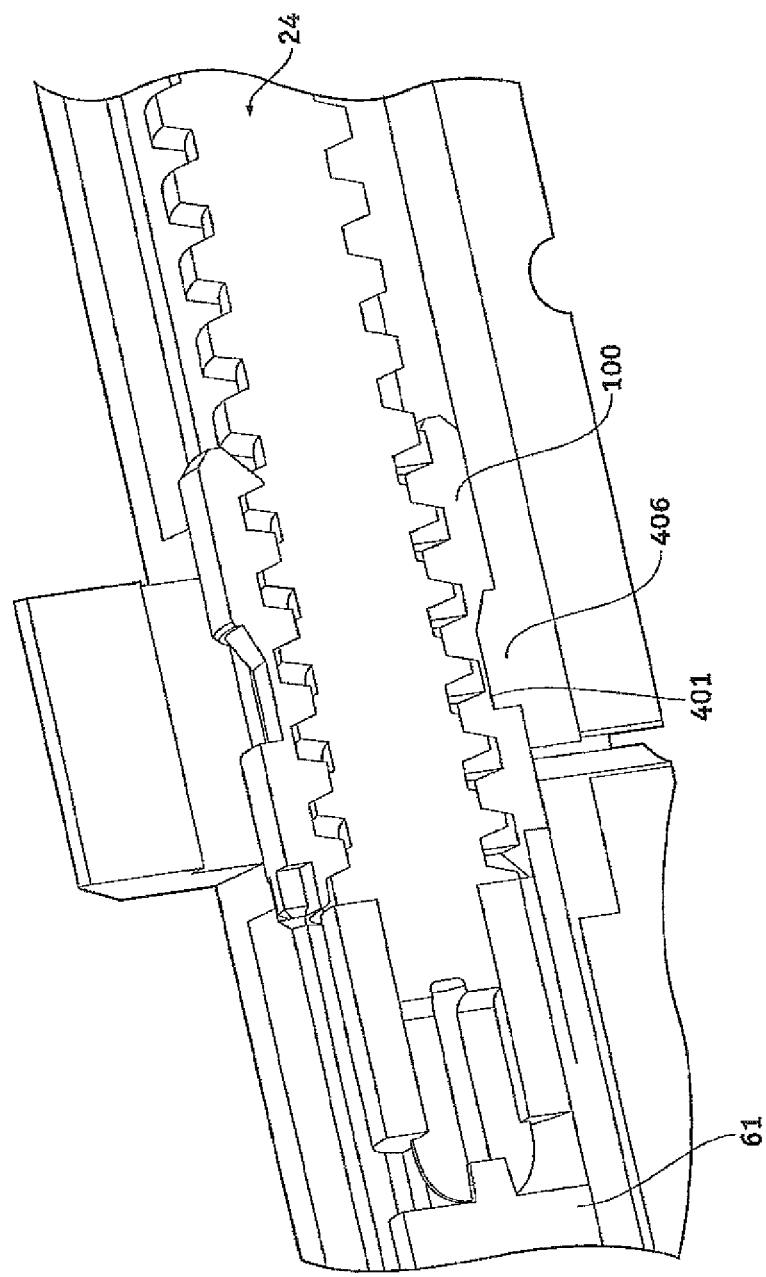
FIG. 33A is a cross-sectional view of a nut lock according to an embodiment.

The detents are one way snaps (cantilever snaps) that provide the strength to prevent the pushrod assembly 60 from being pulled back from the second detent 406 (see FIG. 33A). The proximal detent(s) 407 also provide biasing for the proximal end of the plunger 24 as it is advanced longitudinally or rotated and provide a little resistance (see FIG. 33B). The proximal detents 407 may be the same or similar to the second detent 406. The proximal detents 407 may have a different configuration or shape from the second detent 406. The detents may be of any shape or size suitable for its function.

Safety Detent for Plunger Threads

Figure 34:
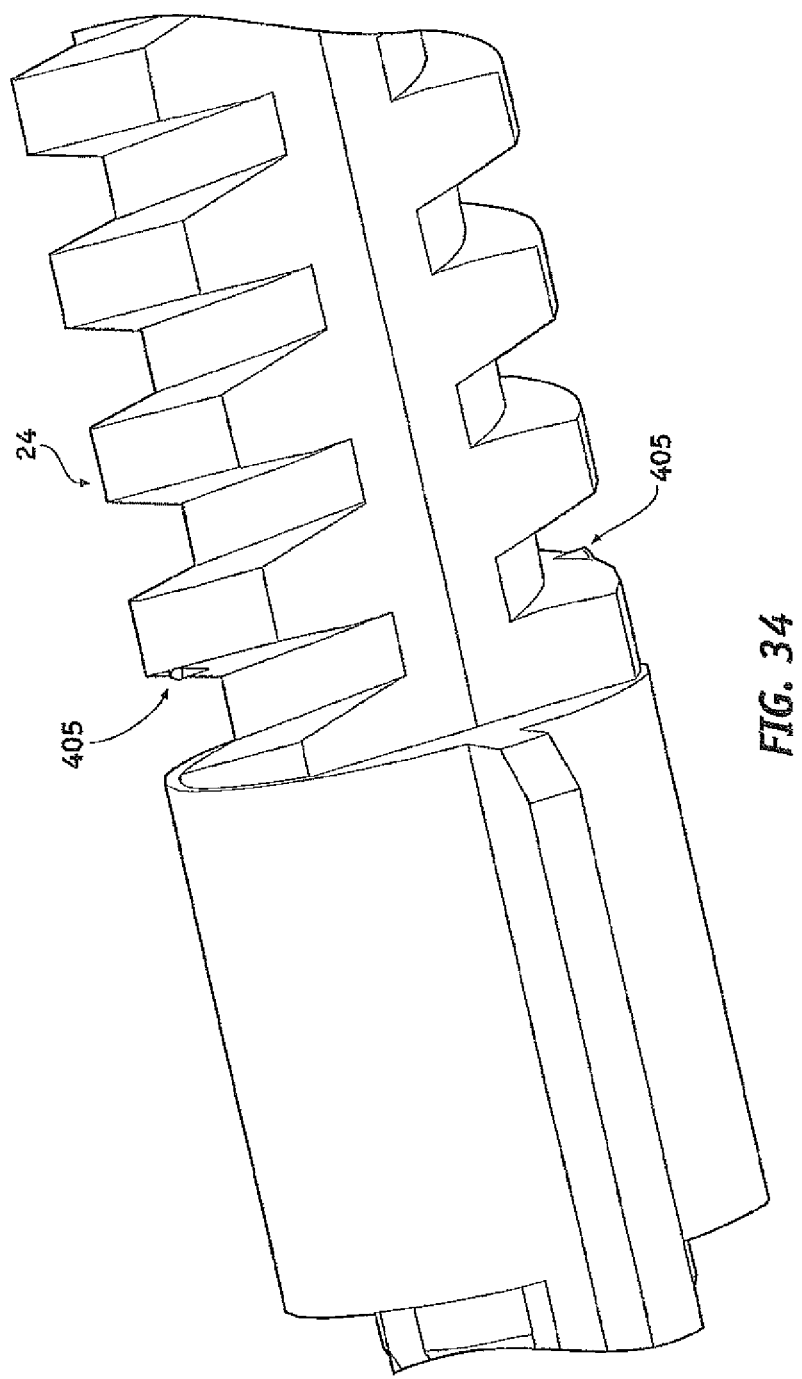
FIG. 34 is a perspective view of a detent safety embodiment.

According to an embodiment, to help prevent advancing the pushrod with rotation of plunger 24 until desired, detents 405 are added to the plunger. Detents 405 are located on the distal end or portion of plunger 24. According to an embodiment, the detents are located within the first two to three threads of plunger 24. FIG. 34 illustrates detents 405 at the distal end or portion of plunger 24. The number of detents can range between 1-6, preferably 4.

All references cited herein are hereby incorporated by reference in their entirety including any references cited therein.

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that described above which are fully equivalent. Consequently, it is not the intention to limit this invention to the particular embodiments disclosed. On the contrary, the intention is to cover modifications and alternate constructions coming within the spirit and scope of the invention as generally expressed by the following claims, which particularly point out and distinctly claim the subject matter of the invention.

The invention claimed is:
1. An insertion system, comprising:
 a handpiece having a longitudinal axis, a distal end, and a proximal end,
  wherein the handpiece comprises a body;
   wherein the body comprises a slot near the distal end that is parallel to the longitudinal axis;
 a cartridge comprising a delivery tube at a distal end;
  wherein the cartridge is configured and dimensioned to couple with the distal end of the handpiece;
 a pin,
  wherein the pin is configured and dimensioned to couple with the slot and move along a distance within the slot; and
 a cap comprising a snap;

wherein the cap is configured and dimensioned to couple with the distal end of the cartridge; and wherein the snap is configured and dimensioned to couple with the pin.

2. The insertion system of claim 1, wherein the pin comprises a top and a stem and wherein the stem couples with the slot and is configured and dimensioned to move within the slot.

3. The insertion system of claim 2, wherein at least a portion of the stem is offset from a centerline of the pin.

4. The insertion system of claim 1, wherein the snap comprises a keyway, wherein the keyway is configured and dimensioned to couple with the pin.

5. The insertion system of claim 1, wherein the cap further comprises one or more ports.

6. The insertion system of claim 5, wherein the one or more ports comprise a funnel shape.

7. The insertion system of claim 5, wherein the cap comprises a first port, wherein the first port comprises a funnel shape, wherein the first port is located at a distal end of the cap and is configured and dimensioned to couple with a lumen at a distal end of the cartridge to enable insertion of a fluid into the lumen of the insertion system.

8. The insertion system of claim 7, wherein the cap comprises a top, a bottom, a first side and a second side, wherein the cap further comprises a second port, wherein the second port comprises a funnel shape and is located on the bottom of the cap and is configured and dimensioned to couple with an opening in the insertion system to enable insertion of a fluid into the insertion system.

9. The insertion system of claim 1, wherein the cap further comprises one or more windows.

10. The insertion system of claim 9, wherein at least one window comprises a fill indicator.

11. The insertion system of claim 9, wherein at least one window is located on a bottom of the cap and wherein the window runs along at least a portion of a longitudinal axis of the cap.

12. The insertion system of claim 1, wherein the cap further comprises a first lock and a second lock, wherein the first lock is located on a first side and the second lock is located on a second side of the cap, and wherein the first and second side are on opposite sides of the cap.

13. The insertion system of claim 1, wherein the cap further comprises at least two finger grips along at least a portion of a longitudinal axis of the cap and wherein the finger grips are located on opposite sides of the cap.

14. The insertion system of claim 1, wherein the cap is made of a clear or translucent material.

15. The insertion system of claim 1, wherein the handpiece is made of a clear or translucent material.

16. The insertion system of claim 1, wherein the pin comprises a top and a stem.

17. The insertion system of claim 16, wherein the top and the stem are configured and dimensioned to allow the pin to couple with the snap in a proper orientation.

18. A method for sweeping a haptic of an IOL, comprising:

providing an insertion system, a cap, and a pin,
wherein the insertion system comprises an IOL having a haptic, a cartridge comprising a delivery tube at a distal end and a handpiece having a longitudinal axis, a distal end, and a proximal end;
wherein the handpiece comprises a body and the handpiece body comprises a slot near the distal end that is parallel to the longitudinal axis; and
wherein the cartridge is configured and dimensioned to couple with the distal end of the handpiece;
wherein the cap comprises a body having a longitudinal axis, a distal end, and a proximal end, and a locking mechanism, wherein the cap body comprises a snap at or near the proximal end, and wherein the snap is configured and dimensioned to couple with the pin;
wherein the pin comprises a top and a stem and wherein the stem is configured and dimensioned to couple with the slot and is configured and dimensioned to move within the slot;
wherein the cap is coupled with a distal end of the insertion system;

deactivating the locking mechanism;
advancing the cap in a distal direction to move the pin coupled with the cap along the slot from a first position to a second position; and
removing the cap from the insertion system, thereby sweeping the haptic in a distal direction.

19. The method of claim 18, wherein the locking mechanism comprises a first lock and a second lock, wherein the first lock is located on a first side and the second lock is located on a second side of the cap, and wherein the first side and second side are on opposite sides of the cap.

\* \* \* \* \*